(12) United States Patent
Goldspink et al.

(10) Patent No.: US 9,919,031 B2
(45) Date of Patent: Mar. 20, 2018

(54) USE OF THE INSULIN-LIKE-GROWTH FACTOR 1 SPLICE VARIANT MGF FOR THE PREVENTION OF MYOCARDIAL DAMAGE

(71) Applicants: Geoffrey Goldspink, Hartfordshire (GB); Paul Goldspink, Northfield, IL (US)

(72) Inventors: Geoffrey Goldspink, Hartfordshire (GB); Paul Goldspink, Northfield, IL (US)

(73) Assignee: THE BOARD OF TRUSTEES OF UNIVERSITY OF ILLINOIS, Urbana, IL (US)

( * ) Notice: Subject to any disclaimer, the term of this patent is extended or adjusted under 35 U.S.C. 154(b) by 0 days.

(21) Appl. No.: 13/624,365

(22) Filed: Sep. 21, 2012

(65) Prior Publication Data

US 2013/0210723 A1 Aug. 15, 2013

Related U.S. Application Data

(60) Continuation of application No. 13/362,987, filed on Jan. 31, 2012, now abandoned, which is a continuation of application No. 11/723,493, filed on Mar. 20, 2007, now abandoned, which is a division of application No. 10/504,087, filed as application No. PCT/GB03/00537 on Feb. 6, 2003, now Pat. No. 7,452,877.

(30) Foreign Application Priority Data

Feb. 7, 2002 (GB) .................................... 0202906.4

(51) Int. Cl.
*A61K 38/18* (2006.01)
*A61K 38/30* (2006.01)
*A61K 31/7088* (2006.01)

(52) U.S. Cl.
CPC .......... *A61K 38/18* (2013.01); *A61K 31/7088* (2013.01); *A61K 38/30* (2013.01)

(58) Field of Classification Search
None
See application file for complete search history.

(56) References Cited

U.S. PATENT DOCUMENTS

| | | |
|---|---|---|
| 4,068,224 A | 1/1978 | Bechtle et al. |
| 5,068,224 A | 11/1991 | Fryklund et al. |
| 5,194,596 A | 3/1993 | Tischer et al. |
| 5,350,836 A | 9/1994 | Kopchick et al. |
| 5,468,478 A | 11/1995 | Saifer et al. |
| 5,650,496 A | 7/1997 | Brierley et al. |
| 5,714,460 A | 2/1998 | Gluckman et al. |
| 5,730,990 A | 3/1998 | Greenwald et al. |
| 5,776,897 A | 7/1998 | Lewis et al. |
| 5,808,096 A | 9/1998 | Zalipsky |
| 5,840,900 A | 11/1998 | Greenwald et al. |
| 5,861,373 A | 1/1999 | Gluckman et al. |
| 6,214,966 B1 | 4/2001 | Harris |
| 6,221,842 B1 | 4/2001 | Goldspink |
| 6,821,946 B2 | 11/2004 | Goldspink et al. |
| 2002/0083477 A1* | 6/2002 | Goldspink ............. A61K 38/30 800/8 |
| 2005/0048028 A1 | 3/2005 | Goldspink et al. |
| 2006/0211606 A1 | 9/2006 | Goldspink et al. |

FOREIGN PATENT DOCUMENTS

| | | |
|---|---|---|
| EP | 0229750 A2 | 7/1987 |
| EP | 0308386 A1 | 3/1989 |
| EP | 0566641 A1 | 10/1993 |
| EP | 0597033 A1 | 5/1994 |
| WO | WO-1986/04145 A1 | 7/1986 |
| WO | WO-1991/01758 A1 | 2/1991 |
| WO | WO-1992/11865 A1 | 7/1992 |
| WO | WO-1992/19256 A1 | 11/1992 |
| WO | WO-1993/09236 A1 | 5/1993 |
| WO | WO-1993/10806 A1 | 6/1993 |
| WO | WO-1995/13290 A1 | 5/1995 |
| WO | WO-1997/33997 A1 | 9/1997 |
| WO | WO-1999/55376 A1 | 11/1999 |
| WO | WO-2001/36483 A1 | 5/2001 |
| WO | WO-2001/85781 A2 | 11/2001 |
| WO | WO-2003/068949 A1 | 8/2003 |

OTHER PUBLICATIONS

Hansen et al., Circulation, 2004; 110, No. 17, Suppl. S: 285. 77th Scientific Meeting of the American-Heart-Association. New Orleans, LA, USA. Nov. 7-10, 2004. Amer Heart Assoc.*
Los et al., Circulation, 2008; 118, No. 18, Suppl. 2: S400. 81st Annual Scientific Session of the American-Heart-Association. New Orleans, LA, USA. Nov. 8-12, 2008. Amer Heart Assoc.*
Tokuriki and Tawflik, Current Opinion in Structural Biology 2009, 19: 596-604.*
Phillips, A., J Pharm Pharmacology, 2001; 53: 1169-1174.*
Winkler, Ther. Deliv. 2013; 4: 791-809.*
Ahmed et al., Nerve growth factor enhances peripheral nerve regeneration in non-human primates, Scand. J. Plast. Reconstr. Hand Surg., 33(4):393-401 (1999).
Alila et al., Expression of biologically active human insulin-like growth factor-I following intramuscular injection of a formulated plasmid in rats, Hum. Gene Ther., 8(15):1785-95 (1997).
Apfel et al, Neurotrophic factors in the treatment, Symposium on Growth factors as drugs for neurological and sensory disorders held at the Ciba Foundation, pp. 98-112 (1995).
Bork et al., Go hunting in sequence databases but watch out for the traps, Trends Genet., 12(10):425-7 (1996).
Bork, Powers and pitfalls in sequence analysis: the 70% hurdle, Genome Res., 10(4):398-400 (2000).
Brenner, Errors in genome annotation, Trends Genet., 15(4):132-3 (1999).

(Continued)

*Primary Examiner* — Christina M Borgeest
(74) *Attorney, Agent, or Firm* — Klintworth & Rozenblat IP LLP

(57) ABSTRACT

The invention relates to the use of a Mechano Growth Factor (MGF) polypeptide or a polynucleotide encoding an MGF polypeptide in the manufacture of a medicament for the prevention or limitation of myocardial damage in response to ischemia or mechanical overload of the heart by preventing or limiting apoptosis in the myocardium.

9 Claims, 20 Drawing Sheets

(56) References Cited

OTHER PUBLICATIONS

Buerke et al., Cardioprotective effect of insulin-like growth factor I in myocardial ischemia followed by reperfusion, Proc. Natl. Acad. Sci. USA, 92:8031-8035 (1995).
Cai et al., High levels of dietary advanced glycation end products transform low-density lipoprotein into a potent redox-sensitive mitogen-activated protein kinase stimulant in diabetic patients, Circulation., 110(3):285-91 (2004).
Caroni et al., Role of muscle insulin-like growth factors in nerve sprouting: suppression of terminal sprouting in paralyzed muscle by IGF-binding protein 4, J. Cell. Biol., 125(4):893-902 (1994).
Caroni et al., Signaling by insulin-like growth factors in paralyzed skeletal muscle: rapid induction of IGF1 expression in muscle fibers and prevention of interstitial cell proliferation by IGF-BP5 and IGF-BP4, J. Neurosci., 14(5):3378-88 (1994).
Carpenter et al., Mechano-growth factor reduces loss of cardiac function in acute myocardial infarction, Heart Lung Circ., 17(1):33-9 (2008).
Chew et al., An alternatively spliced human insulin-like growth factor-I transcript with hepatic tissue expression that diverts away from the mitogenic IBE1 peptide, Endocrinology, 136(5):1939-44 (1995).
De Bari et al., Skeletal muscle repair by adult human mesenchymal stem cells from synovial membrane, J. Cell. Biol., 160(6):909-18 (2003).
Declaration of Geoffrey Goldspink filed in connection with U.S. Appl. No 10/130,211, 2005.
DeVol et al., Activation of insulin-like growth factor gene expression during work-induced skeletal muscle growth, Am. J. Physiol., 259(1):E89-95 (1990).
Dillmann et al., Heat shock proteins in myocardial stress, Z Kardiol., 84 Suppl 4:87-90 (1995).
Ding et al., Left ventricular hypertrophy in ascending aortic stenosis mice: anoikis and the progression to early failure, Circulation, 101:2854-62 (2000).
Dirksen et al., Reperfusion injury in humans: a review of clinical trials on reperfusion injury inhibitory strategies, Cardiovasc. Res., 74(3):343-55 (2007).
Dluzniewska et al, The FASEB Journal, 1-21 (2005).
Dluzniewska et al., A strong neuroprotective effect of the autonomous C-terminal peptide of IGF-1 Ec (MGF) in brain ischemia, FASEB J., 19(13):1896-8 (2005).
Doerks et al., Protein annotation: detective work for function prediction, Trends Genet., 14(6):248-50 (1998).
Donoghue et al., A muscle-specific enhancer is located at the 3' end of the myosin light-chain 1/3 gene locus, Genes Dev., 2(12B):1779-90 (1988).
Doréet al., Rediscovering an old friend, IGF-I: potential use in the treatment of neurodegenerative diseases, Trends Neurosci., 20(8):326-31 (1997).
Edwall et al., Induction of insulin-like growth factor I messenger ribonucleic acid during regeneration of rat skeletal muscle, Endocrinology, 124(2):820-5 (1989).
Fazio et al., A preliminary study of growth hormone in the treatment of dilated cardiomyopathy, N. Engl. J. Med., 334:809-14 (1996).
Fischer, The design, synthesis and application of stereochemical and directional peptide isomers: a critical review, Curr. Protein Pept. Sci., 4(5):339-56 (2003).
Gauvry et al., The characterisation of the 5' regulatory region of a temperature-induced myosin-heavy-chain gene associated with myotomal muscle growth in the carp, Eur. J. Bichem., 236(3):887-94 (1996).
Goldspink et al., Effects of activity on growth factor expression, Int. J. Sport Nutr. Exerc. Metab., 11:S21-7 (2001).
Goldspink et al., Gene expression in skeletal muscle in response to stretch and force generation, Am. J. Physiol., 262(3):R356-63 (1992).
Goldspink et al., Local growth regulation is associated with an isoform of IGF-I that is expressed in normal muscles but not in dystrophic muscles, J. Physiol., 495:162-163 (1996).
Goldspink et al., Localization of cardiac (alpha)-myosin heavy chain mRNA is regulated by its 3' untranslated region via mechanical activity and translational block, J. Cell. Sci., 110:2969-78 (1997).
Goldspink et al., Muscle growth in response to mechanical stimuli, Am. J. Physiol., 268(2):E288-97 (1995).
Goldspink et al., The effect of hypokinesia and hypodynamia on protein turnover and the growth of four skeletal muscles of the rat, Pflugers Arch., 407(3):333-40 (1986).
Goldspink, Changes in muscle mass and phenotype and the expression of autocrine and systemic growth factors by muscle in response to stretch and overload, Journal of Anatomy, 194(3):323-34 (1999).
Hameed et al., Expression of IGF-I splice variants in young and old human skeletal muscle after high resistance exercise, J. Physiol., 547(1):247-54 (2003).
Hameed et al., The effect of recombinant human growth hormone and resistance training on IGF-I mRNA expression in the muscles of elderly men, J. Physiol., 555(Pt 1):231-40 (2004).
Han et al., Cellular localization of somatomedin (insulin-like growth factor) messenger RNA in the human fetus, Science, 236(4798):193-7 (1987).
Hazari et al., A new resorbable wrap-around implant as an alternative nerve repair technique, J. Hand Surg. Br., 24(3):291-5 (1999).
Hazari et al., A resorbable nerve conduit as an alternative to nerve autograft in nerve gap repair, Br. J. Plast. Surg., 52(8):653-7 (1999).
Hii et al., Expression and splicing of the insulin-like growth factor gene in rodent muscle is associated with muscle satellite (stem) cell activation following local tissue damage, J. Physiol., 549(Pt 2):409-18 (2003).
Hobson et al., VEGF enhances intraneural angiogenesis and improves nerve regeneration after axotomy, J. Anat., 197(4):591-605 (2000).
Hope, Implant that could make damaged nerves work again, Daily Mail, 1 (1999).
Ido et al., Prevention of vascular and neural dysfunction in diabetic rats by C-peptide, Science, 277(5325):563-6 (1997).
International Search Report dated Jul. 17 2006, issued in connection with PCT/GB2006/001012.
Jackowski, Neural injury repair: hope for the future as barriers to effective CNS regeneration become clearer, Br. J. Neurosurg., 9(3):303-17 (1995).
Jansen et al., Identification of multiple transcription start sites in the human insulin-like growth factor-I gene, Mol. Cell. Endocrinol., 78(1-2):115-25 (1991).
Jansen et al., Sequence of cDNA encoding human insulin-like growth factor I precursor, Nature, 306(5943):609-11 (1983).
Johnson et al., Rescue of Injured Adult, Society for Neuroscience Abstracts, 26:Abstract No.-792.3, XP001029877 (2000).
Kaspar et al., Synergy of insulin-like growth factor-1 and exercise in amyotrophic lateral sclerosis, Ann. Neurol., 57(5):649-55 (2005).
Kimes et al., Properties of a clonal muscle cell line from rat heart, Exp. Cell. Res., 98(2):367-381 (1976).
Kotlyar et al., Insulin-like growth factor I and II preserve myocardial structure in postinfarct swine, Heart, 86(6):693-700 (2001).
Lowe et al., Distribution and regulation of rat insulin-like growth factor I messenger ribonucleic acids encoding alternative carboxyterminal E-peptides: evidence for differential processing and regulation in liver, Mol. Endocrinol., 2(6):528-35 (1988).
Lundborg et al., Tubular versus conventional repair of median and ulnar nerves in the human forearm: early results from a prospective, randomized, clinical study, J. Hand Surg. Am., 22(1):99-106 (1997).
Matthews et al., Changes in IGFs in cardiac tissue following myocardial infarction, J. Endocrinol, 163(3):433-45 (1999).
Mañes et al., Functional epitope mapping of insulin-like growth factor I (IGF-I) by anti-IGF-I monoclonal antibodies, Endocrinology, 138(3):905-15 (1997).
McKoy et al., Expression of insulin growth factor-1 splice variants and structural genes in rabbit skeletal muscle induced by stretch and stimulation, J. Physiol., 516.2:583-92 (1999).
McMahon et al. Euro Heart J. 2004; 24: 497.
Mockridge et al, IGF-1 Regulates Cardiac Fibroblast Apoptosis Induced by Osmotic Stress, Biochemical and Biophysical Research Communications, 273(1):322-327 (2000).

(56) References Cited

OTHER PUBLICATIONS

Morishita et al., Pluronic F-127 gels incorporating highly purified unsaturated fatty acids for buccal delivery of insulin, Int. J. Pharm., 212(2):289-93 (2001).
Neville et al., Modular elements of the MLC 1f/3f locus confer fiber-specific transcription regulation in transgenic mice, Dev. Genetics, 19(2):157-62 (1996).
Ngo et al. Computational Complexity, Protein Structure Prediction, and the Levinthal Paradox, The Protein Folding Problem and Teriary Structure Prediction, #14:491-495 (1994).
Phillips, The challenge of gene therapy and DNA delivery, J. Pharm. Pharmacology, 53(9):1169-74 (2001).
Phoenix Pharmaceuticals, Inc., MGF, The C-terminal peptide of Mechano-Growth Factor, an Alternatively spliced variant of insulin-like growth factor 1 (IGF-1), pp. 1-11, printed on Nov. 30, 2005 from http://www.phoenixpeptide.com.
Phoenix Pharmaceuticals, Inc., pp. 1-2 , printed on Nov. 30, 2005 from http://www.phoenixpeptide.com.
Phoenix Pharmaceuticals, Inc., pp. 1-5 , printed on Feb. 28, 2006 from http://www.phoenixpeptide.com.
Phoenix Pharmaceuticals, pp. 1-3, printed on Nov. 30, 2005 from http://www.phoenixpeptide.com.
Reeck et al., "Homology" in proteins and nucleic acids: A terminology muddle and a way out of it. Cell, 50: 667 (1987).
Response of Jul. 20, 2004 to EPO in response to Examination Report of Sep. 24, 2003, filed in connection with European Patent Application No. 97906296.5.
Rotwein et al., Organization and sequence of the human insulin-like growth factor I gene. Alternative RNA processing produces two insulin-like growth factor I precursor peptides, J. Biol. Chem., 261(11):4828-32 (1986).
Rotwein, Two insulin-like growth factor I messenger RNAs are expressed in human liver, Proc. Natl. Acad. Sci. USA, 83(1):77-81 (1986).
Rowland, Diseases of the motor unit: the motor neuron, peripheral nerve, and muscle, Principles of Neural Science, 196-208 (1985).
Saragovi et al., Small molecule and protein-based neurotrophic ligands: agonists and antagonists as therapeutic agents , Exp. Opin. Ther. Patents., 9(6):737-751 (1999).
Siegfried et al., A mitogenic peptide amide encoded within the E peptide domain of the insulin-like growth factor IB prohormone, Proc. Natl. Acad. Sci. USA, 89(17):8107-11 (1992).
Simon et al., Differential effects of NT-3 on reinnervation of the fast extensor digitorum longus (EDL) and the slow soleus muscle of rat, Eur. J. Neurosci., 12(3):863-71 (2000).
Skarli et al, J. Physiol. 509.8, 192.8 (1998).
Skolnick et al., From genes to protein structure and function: novel applications of computational approaches in the genomic era, Trends Biotechnol., 18(1):34-9 (2000).
Smith et al., The challenges of genome sequence annotation or "the devil is in the details", Nat. Biotechnol., 15(12):1222-3 (1997).
Spatola, Chemistry and Biochemistry of Amino Acids, Peptides and Proteins, 267-357 (1983).
Sterne et al., Neurotrophin-3 delivered locally via fibronectin mats enhances peripheral nerve regeneration, Eur. J. Neurosci., 9(7):1388-96 (1997).
Sterne et al., Neurotrophin-3-enhanced nerve regeneration selectively improves recovery of muscle fibers expressing myosin heavy chains 2b, J. Cell. Biol., 139(3):709-15 (1997).
Sterne et al., NT-3 modulates NPY expression in primary sensory neurons following peripheral nerve injury, J. Anat. 193:273-81 (1998).
Stewart et al., Growth, differentiation, and survival: multiple physiological functions for insulin-like growth factors, Physiol Rev., 76(4):1005-26 (1996).
Swynghedauw et al., What is wrong with positive inotropic drugs? Lessons from basic science and clinical trials, European Heart Journal Supplements, 4:D43-D49 (2002).
Tan et al, The Problems of Delivering Neuroactive, Symposium on Growth factors as drugs for neurological and sensory disorders held at the Ciba Foundation, pp. 211-239 (1995).
Thoenen et al., Trophic support of motoneurons: physiological, pathophysiological, and therapeutic implications, Exp. Neurol., 124(1):47-55 (1993).
Thuesen et al., Increased myocardial contractility following growth hormone administration in a normal man. An echocardiographic study, Dan. Med. Bull., 35:193-196 (1988).
Tian et al., Recombinant E-peptides of pro-IGF-I have mitogenic activity, Endocrinology, 140(7):3387-90 (1999).
Tobin et al., A novel human insulin-like growth factor I messenger RNA is expressed in normal and tumor cells, Mol. Endocrinol., 4(12):1914-20 (1990).
Tuszynski et al, Somatic gene therapy for nervous, Symposium on Growth factors as drugs for neurological and sensory disorders held at the Ciba Foundation, pp. 85-97 (1995).
Valenzuela et al., Receptor tyrosine kinase specific for the skeletal muscle lineage: expression in embryonic muscle, at the neuromuscular junction, and after injury, Neuron, 15(3):573-84 (1995).
Vaught et al, Potential utility of rhIGF-1, Symposium on Growth factors as drugs fro neurological and sensory disorders held at the Ciba Foundation, pp. 18-38 (1995).
Vejsada et al., Quantitative comparison of the transient rescue effects of neurotrophic factors on axotomized motoneurons in vivo, Eur. J. Neurosci., 7(1):108-15 (1995).
Vejsada et al., Synergistic but transient rescue effects of BDNF and GDNF on axotomized neonatal motoneurons, Neuroscience, 84(1):129-39 (1998).
Veronese, Peptide and protein PEGylation: a review of problems and solutions, Biomaterials, 22(5):405-17 (2001).
Vukicevic et al., Induction of nephrogenic mesenchyme by osteogenic protein 1 (bone morphogenetic protein 7), Proc. Natl. Acad. Sci. USA, 93(17):9021-6 (1996).
Website of Human Genome Project Information, pp. 1-7. www.ornl.gov/hgmis, downloaded Jan. 6, 2006.
Wells, Additivity of mutational effects in proteins, Biochemistry, 29(37):8509-17 (1990).
Whitworth et al., Nerve growth factor enhances nerve regeneration through fibronectin grafts, J. Hand Surg. Br., 21(4):514-22 (1996).
Whitworth et al., Orientated mats of fibronectin as a conduit material for use in peripheral nerve repair, J. Hand Surg. Br., 20(4):429-36 (1995).
Whitworth et al., Targeted delivery of nerve growth factor via fibronectin conduits assists nerve regeneration in control and diabetic rats, Eur. J. Neurosci., 7(11):2220-5 (1995).
Wiberg et al., Primary sensory neuron survival following targeted administration of nerve growth factor to an injured nerve, Scand. J. Plast. Reconstr. Surg. Hand Surg., 33(4):387-92 (1999).
Yamashita et al., Reperfusion-activated Akt kinase prevents apoptosis in transgenic mouse hearts overexpressing insulin-like growth factor-1, Circ. Res., 30;88(6):609-14 (2001).
Yan et al., The use of trophic factors in degenerative motoneuron diseases, Exp. Neurol., 124(1):60-3 (1993).
Yang et al, Cloning and characterization of an IGF-1 isoform expressed in skeletal muscle subjected to stretch, Journal of Muscle Research and Cell Motility, 17(4):487-495 (1996).
Yang et al., Different roles of the IGF-I Ec peptide (MGF) and mature IGF-I in myoblast proliferation and differentiation, FEBS Letters, 522(1-3):156-60 (2002).
Yang et al., Different roles of the IGF-I Ec peptide (MGF) and mature IGF-I in myoblast proliferation and differentiation, FEBS Letters, 580(10):2530 (2006).
Yaoita et al, Significance of apoptosis in the cardiovascular system: significance of apoptosis in ischemic heart diseases, Molecular Cardiovascular Medicine, 2(3):307-313 (2001) (Japanese text with 1 page English language Summary with Hiraki & Associates Caption).

* cited by examiner

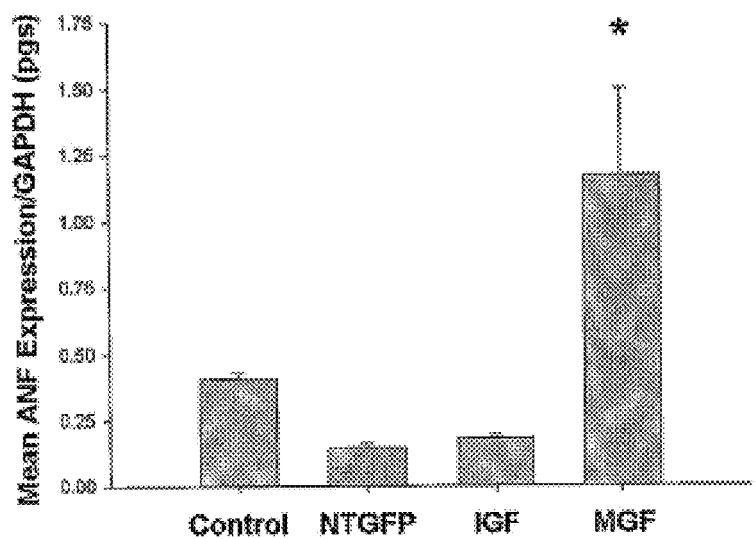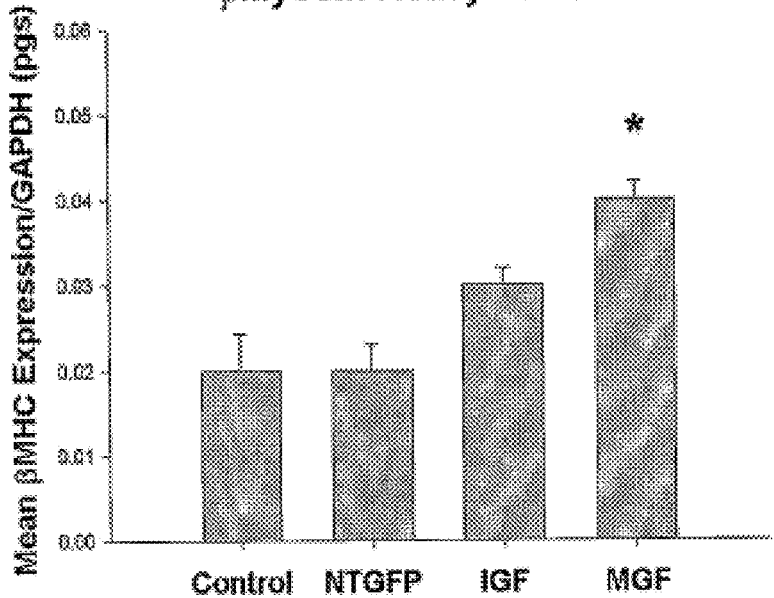
FIGURE 3 cDNA sequence of Human MGF

Exon 3

GGACCGGAGAGACGCTCTGCGGGGCTGAGCTGGTGAGATGCTCTTCAGTTCGTGTGTGGAGACAGGGGCTTTTATTTCAACAAGCCCACAGGGTATGGCTCCAGCAGTCGG

Exon 4

AGGGCGCCTCAGACAGGCATCGTGGATGAGTGCTGCTTCCGGAGCTGTGATCTAAGGAGGCTGGAGATGTATTGCGCACCCCTCAAGCCTGCCAAGTCAGCTCGCTC

TGTCCGTGCCCAGCGCCACACCGACATGCCCAAGACCCAGAAGTATCAGCCCCCATCTACCAACAAGAACACGAAGTCTCAGAGAAGGAAAGGAAGTACATTTGAAG

Exon 5

AACACAAGTAGAGGGAGTGCAGGAAACAAGAACTACAGGATGTAGAAGAAGACCCTTCTGAGGAGTGAAGAAGGACAGGCCACCGCAGGACCCTTTGCTCTGACACAGTTAGTA

Exon 6

CCTAACATTGAATACCGGCCAAAAAATAAGTTTGATCACATTTCAAAGATGGCATTTCCCCAATGAAATACACAAGTAAACAT (SEQ ID NO: 15)

Protein sequence of Human MGF

Exon 4

GlyProGluThrLeuCysGlyAlaGluLeuValAspAlaLeuGlnPheValCysGlyAspArgGlyPheTyrPheAsnLysProThrGlyTyrGlySerSerArg

Exon 5

ArgAlaProGlnThrGlyIleValAspGluCysCysPheArgSerCysAspLeuArgArgLeuGluMetTyrCysAlaProLeuLysProAlaLysSerAlaArgSer

Exon 6

ValArgAlaGlnArgHisThrAspMetProLysThrGlnLysTyrGlnProProSerThrAsnLysAsnThrLysSerGlnArgArgLysGlySerThrPheGlu

GluHisLys (SEQ ID NO: 16)

FIGURE 7 cDNA sequence of Rat MGF

Exon 3
GGACCAGAGACCCTTTGCGGGGCTGAGCTGGTGGACGCTCTTCAGTTCGTGTGTGGACCAAGGGGCTTTTACTTCAACAAGCCCACAGTCTATGGCTCCAGCATTCG Exon 4
GAGGGCACCACAGACGGGCCATTGTGGATGAGTGTTGCTTCCGGAGCTGTGATCTGAGGAGCTGGAGATGTACTGTGTCCGCTGCAAGCCTACAAAGTCAGCTCGTT Exon 5
CCATCCGGGCCCAGCGCCACACTGACATGCCCAAGACTCAGAAGTCCCAGCCCTATCGACACACAAGAAAAAGGAAGCTGCAAAGGAGAAGGAAGTACACTT GAAGAACAAGTAGAGGAAGTGCAGGAAAACAAGACCTACAGAATGTAGGAGGAGCCTCCCGAGGAACAGAAATGCCACGTCACCGCAAGATCCTTTGCTGCTTG Exon 6
GCAACCTGCAAAACATCGAACACCTGCCAAATAATCAATAATGAGTTCAATATCATTTCAGAGATGGGCATTCCCTCAATGAAATACACAAGTAAACATTCCCGGA

ATTC (SEQ ID NO: 17)

Protein sequence of Rat MGF

Exon 3                                                                                          Exon 4
GlyProGluThrLeuCysGlyAlaGluLeuValAspAlaLeuGlnPheValCysGlyProArgGlyPheTyrPheAsnLysProThrValTyrGlySerSerIleArg ArgAlaProGlnThrGlyIleValAspGluCysCysPheArgSerCysAspLeuArgArgLeuGluMetTyrCysValArgCysLysProThrLysSerAlaArg Exon 5                                                                                          Exon 6
SerIleArgAlaGlnArgHisThrAspMetProLysThrGlnLysSerGlnProLeuSerThrHisLysLysArgLysLeuGlnArgArgArgLysGlySerThrLeu GluGluHisLys (SEQ ID NO: 18)

FIGURE 8 cDNA sequence of Rabbit MGF

Exon 3
GGACCGGAGAGACGCTCTGCGGTGCTGAGCTGGTGGATGCTCTTCAGTTCGTGTGTGGAGACAGGGGCTTTTATTTCAACAAGCCCACAGGATACGGCTCCAGCAGTGCGGAGGGCACC Exon 4
TCAGACAGGCATCGTGGATGAGTGCTGCTTCCGGAGCTGTGATCTGAGGAGGCTGGAGATGTACTGTGCACCCCTCAAGCCGGCAAAGGCAGCCCGCTCCGTCCGTGCCCAGCGCC Exon 5
ACACCGACATGCCCAAGACTCAGAAGTATCAGCCTCCATCTACCAACAAGAAAATGAAGTCTCAGAGGAGAAGGAAGTACATTTGAAGAACACAAGTAGAGGGAGTGCAGG Exon 6
AAACAAGAACTACAGGATGTAGGAAGACCCTTCTGAGGAGTGAAGAAGGACAGGCCACCGCAGGACCCCTTTGCTCTGCACAGTTACCTGTAAACATTGGAATACCGGCCAAAAAT

AAGTTTGATCACATTTCAAAGATGGCATTTCCCCAATGAAATACACAAGTAAACATTC (SEQ ID NO: 19)

Protein sequence of Rabbit MGF

Exon 3
GlyProGluThrLeuCysGlyAlaGluLeuValAspAlaLeuGlnPheValCysGlyAspArgGlyPheTyrPheAsnLysProThrGlyTyrGlySerSerSerArgArgAlaPro Exon 5
GlnThrGlyIleValAspGluCysCysPheArgSerCysAspLeuArgArgLeuGluMetTyrCysAlaProLeuLysProAlaLysAlaAlaArgSerValArgAlaGlnArgHis Exon 6
ThrAspMetProLysThrGlnLysTyrGlnProProSerThrAsnLysLysMetLysSerGlnArgArgLysGlySerThrPheGluGluHisLys (SEQ ID NO: 20)

FIGURE 9 cDNA sequence of Human L.IGF-1

Exon 3
GGACCGGAGAGCGCTCTGCGGGGCTGAGCTGGTGAGCTGCTCTTCAGTTCGTGTGTGGAGACAGGGGCTTTTATTTCAACAAGCCCACAGGGTATGGCTCCAGCAGTCGGAGGGGCGCC Exon 4
TCAGACAGGGCATCGTGGATGAGTGCTGCTTCCGGAGCTGTGATCTAAGGAGGCTGGAGATGTATTGCGCACCCCCTCAAGCCTGCCAAGTCAGCTCGCTCTGTCCGTGCCCAGCGCC Exon 6
ACACCGACATGCCAAGACCCAGAGAAGTACATTTGAAGAACGCAAGTAGAGGAGTGCAGGAAACAAGAACTACAGGATGTAG (SEQ ID NO: 21)

Protein sequence of Human L.IGF-1

Exon 3                                                                                              Exon 4
GlyProGluThrLeuCysGlyAlaGluLeuValAspAlaLeuGlnPheValCysGlyAspArgGlyPheTyrPheAsnLysProThrGlyTyrGlySerSerArgArgAlaPro GlnThrGlyIleValAspGluCysCysPheArgSerCysAspLeuArgArgLeuGluMetTyrCysAlaProLeuLysProAlaLysSerAlaArgSerValArgAlaGlnArgHis Exon 6
ThrAspMetProLysThrGlnLysGluValHisLeuLysAsnAlaSerArgGlySerAlaArgSerArgGlySerAlaArgSerValArgAlaGlnArgAlaGlnArgAlaArgMet (SEQ ID NO: 22)

FIGURE 10 cDNA sequence of Rat L.IGF-1

Exon 3  
GGACCAGAGACCCTTTGCGGGGGCTGAGCTGGTGGACGCGCTCTTCAGTTCGTGTGTGGACCAAGGGGCTTTTACTTCAACAAGCCCACAGTCTATGGCTCCAGCATTCGGAGGGCACC Exon 4

ACAGACGGGCATTGTGGATGAGTGTTGCTTCCGGAGCTGTGATCTGAGGAGGCTGGAGATGTACTGTGTCCGCTGCAAGCCTACAAAGTCAGCTCGTTCCATCGGGCCCAGCGCC

Exon 6  
ACACTGACATGCCCAAGACTCAGAAGGAAGTACACTTGAAGAACACAAGTAGAGGAAGTGCAGGAAACAAGACCTACAGAGAATGTAGGAGAGCCTCCCGAGGAACAGAGAAATGCCA CGTCACCGCAAGATCCTTTGCTGCTTGAGCAACCTGCAAAACATCGGAACACCTGCCAAATATCAATAATGAGTTCAATATCATTCAGAGATGGGCATTCCCTCAATGAAATAC

ACAAGTAAACATTCCCGGAATTC (SEQ ID NO: 23)

Protein sequence of Rat L.IGF-1

Exon 3  
GlyProGluThrLeuCysGlyAlaGluLeuValAspAlaLeuGlnPheValCysGlyProArgGlyPheTyrPheAsnLysProThrValTyrGlySerSerIleArgArgAla Exon 4  
ProGlnThrGlyIleValAspGluCysCysPheArgSerCysAspLeuArgArgLeuGluMetTyrCysValArgCysLysProThrLysSerAlaArgSerIleArgArgAlaGlnArg Exon 6  
HisThrAspMetProLysThrGlnLysGluValHisLeuLysAsnThrSerArgGlySerAlaGlyAsnLysThrTyrArgMet (SEQ ID NO: 24)

FIGURE 11 cDNA sequence of Rabbit L.IGF-1

Exon 3
GGACCGGAGACGCTCTGCGGTGCTGAGCTGGTGGATGCTCTTCAGTTCGTCGTGTGGAGACAGGGGCTTTTATTTCAACAAGCCCACAGGATACGGCTCCAGCAGTCGGAGGGCACC Exon 4
TCAGACAGGCATCGTCGTGCTGCTCCGGAGCTGTGATGAGTGCTGCTTCCGGAGCTGTGATCTGAGAGGCCTGGAGACGCTGTGCACCCCTCAAGCCAGCCCGCAAAGGCAGCCCCAGCGCC Exon 6
ACACCGACATGCCCAAGACTCAGAAGAAGTACATTTGAAGAACAAGAGGGAGTGCAGGAGAAACAAGAACTACAGGATGTAGGAAGACCCTTCTGAGGAGTGAAGAAGGACA GGCCACCGCCAGGACCCTTTGCTCTGCACAGTTACCTGTAAACATTGAATACCGGCCAAAAAAATAAGTTTGATCACATTTCAAAGATGGCATTTCCCCAATGAAATACACAAGTA

AACATTC (SEQ ID NO: 25)

Protein sequence of Rabbit L.IGF-1

Exon 3
GlyProGluThrLeuCysGlyAlaGlnPheValCysGlyAspArgGlyPheTyrPheAsnLysProThrGlyTyrGlySerSerSerArgArgAlaPro Exon 4
GlnThrGlyIleValAspGluCysCysPheArgSerCysAspLeuArgArgLeuGluMetTyrCysAlaProLeuLysProAlaLysSerAlaArgSerValArgAlaArgGlnArgHis Exon 6
ThrAspMetProLysThrGlnLysGluValHisLeuLysAsnThrSerArgGlySerAlaGlyAsnLysAsnTyrArgMet (SEQ ID NO: 16)

Exon 4

| | | | | | | | | | | | | | | | | | | | | | | | |
|---|---|---|---|---|---|---|---|---|---|---|---|---|---|---|---|---|---|---|---|---|---|---|---|
| Hu MGF  | A | sn | Lys | Pro | Thr | Gly | Tyr | Gly | Ser | Ser | Ser | Arg | Arg | Ala | Pro | Gln | Thr | Gly | Ile | Val | Asp | Glu | Cys | Cys Phe |
| Rat MGF | A | sn | Lys | Pro | Thr | Val | Tyr | Gly | Ser | Ile | Ser | Arg | Arg | Ala | Pro | Gln | Thr | Gly | Ile | Val | Asp | Glu | Cys | Cys Phe |
| Rab MGF | A | sn | Lys | Pro | Thr | Gly | Tyr | Gly | Ser | Ser | Ser | Arg | Arg | Ala | Pro | Gln | Thr | Gly | Ile | Val | Asp | Glu | Cys | Cys Phe |
| Hu IGF  | A | sn | Lys | Pro | Thr | Gly | Tyr | Gly | Ser | Ser | Ser | Arg | Arg | Ala | Pro | Gln | Thr | Gly | Ile | Val | Asp | Glu | Cys | Cys Phe |
| Rat IGF | A | sn | Lys | Pro | Thr | Val | Tyr | Gly | Ser | Ile | Ser | Arg | Arg | Ala | Pro | Gln | Thr | Gly | Ile | Val | Asp | Glu | Cys | Cys Phe |
| Rab IGF | A | sn | Lys | Pro | Thr | Gly | Tyr | Gly | Ser | Ser | Ser | Arg | Arg | Ala | Pro | Gln | Thr | Gly | Ile | Val | Asp | Glu | Cys | Cys Phe |

| | | | | | | | | | | | | | | | | | | | | |
|---|---|---|---|---|---|---|---|---|---|---|---|---|---|---|---|---|---|---|---|---|
| Hu MGF  | Arg | Ser | Cys | Asp | Leu | Arg | Arg | Leu | Glu | Met | Tyr | Cys | Ala | Pro | Leu | Lys | Pro | Ala | Lys | Ser | Ala Arg Ser Val |
| Rat MGF | Arg | Ser | Cys | Asp | Leu | Arg | Arg | Leu | Glu | Met | Tyr | Cys | Val | Arg | Cys | Lys | Pro | Thr | Lys | Ser | Ala Arg Ser Ile |
| Rab MGF | Arg | Ser | Cys | Asp | Leu | Arg | Arg | Leu | Glu | Met | Tyr | Cys | Ala | Pro | Leu | Lys | Pro | Ala | Lys | Ser | Ala Arg Ser Val |
| Hu IGF  | Arg | Ser | Cys | Asp | Leu | Arg | Arg | Leu | Glu | Met | Tyr | Cys | Ala | Pro | Leu | Lys | Pro | Ala | Lys | Ser | Ala Arg Ser Val |
| Rat IGF | Arg | Ser | Cys | Asp | Leu | Arg | Arg | Leu | Glu | Met | Tyr | Cys | Ala | Pro | Leu | Lys | Pro | Ala | Ala | Lys | Ser Arg Ser Ile |
| Rab IGF | Arg | Ser | Cys | Asp | Leu | Arg | Arg | Leu | Glu | Met | Tyr | Cys | Ala | Pro | Leu | Lys | Pro | Ala | Ala | Lys | Ser Arg Ser Val |

Exon 5

| | | | | | | | | | | | | | | | | | |
|---|---|---|---|---|---|---|---|---|---|---|---|---|---|---|---|---|---|
| Hu MGF  | Arg | Ala | Gln | Arg | His | Thr | Asp | Met | Pro | Lys | Thr | Gln | Lys | Tyr | Gln | Pro | Pro | Ser Thr Asn Lys Asn Thr Lys |
| Rat MGF | Arg | Ala | Gln | Arg | His | Thr | Asp | Met | Pro | Lys | Thr | Gln | Lys | Ser | Gln | Pro | Leu | Ser Thr His Lys Lys Arg Lys |
| Rab MGF | Arg | Ala | Gln | Arg | His | Thr | Asp | Met | Pro | Lys | Thr | Gln | Lys | Tyr | Gln | Pro | Pro | Ser Thr Asn Lys Lys Met Lys |
| Hu IGF  | Arg | Ala | Gln | Arg | His | Thr | Asp | Met | Pro | Lys | Thr | Gln | Lys | — | — | — | — | — |
| Rat IGF | Arg | Ala | Gln | Arg | His | Thr | Asp | Met | Pro | Lys | Thr | Gln | Lys | — | — | — | — | — |
| Rab IGF | Arg | Ala | Gln | Arg | His | Thr | Asp | Met | Pro | Lys | Thr | Gln | Lys | — | — | — | — | — |

Exon 6

| | | | | | | | | | | | | | | | | | | | | | | |
|---|---|---|---|---|---|---|---|---|---|---|---|---|---|---|---|---|---|---|---|---|---|---|
| Hu MGF  | Ser | Gln | Arg | Arg | Lys | G | ly | Ser | Thr | Phe | Glu | Glu | His | Lys | | | | | | | | | |
| Rat MGF | Leu | Gln | Arg | Arg | Lys | G | ly | Ser | Thr | Leu | Glu | Glu | His | Lys | | | | | | | | | |
| Rab MGF | Ser | Gln | Arg | Arg | Lys | G | ly | Ser | Thr | Phe | Glu | Glu | His | Lys | | | | | | | | | |
| Hu IGF  | — | — | — | — | — | | | Glu | Val | His | Leu | Lys | Asn | Ala | Ser | Arg | Gly | Ser | Ala | Gly | Asn | Lys | Asn Tyr Arg M |
| Rat IGF | — | — | — | — | — | | | Glu | Val | His | Leu | Lys | Asn | Ala | Ser | Arg | Gly | Ser | Ala | Gly | Asn | Lys | Thr Tyr Arg M |
| Rab IGF | — | — | — | — | — | | | Glu | Val | His | Leu | Lys | Asn | Thr | Ser | Arg | Gly | Ser | Ala | Gly | Asn | Lys | Asn Tyr Arg M |

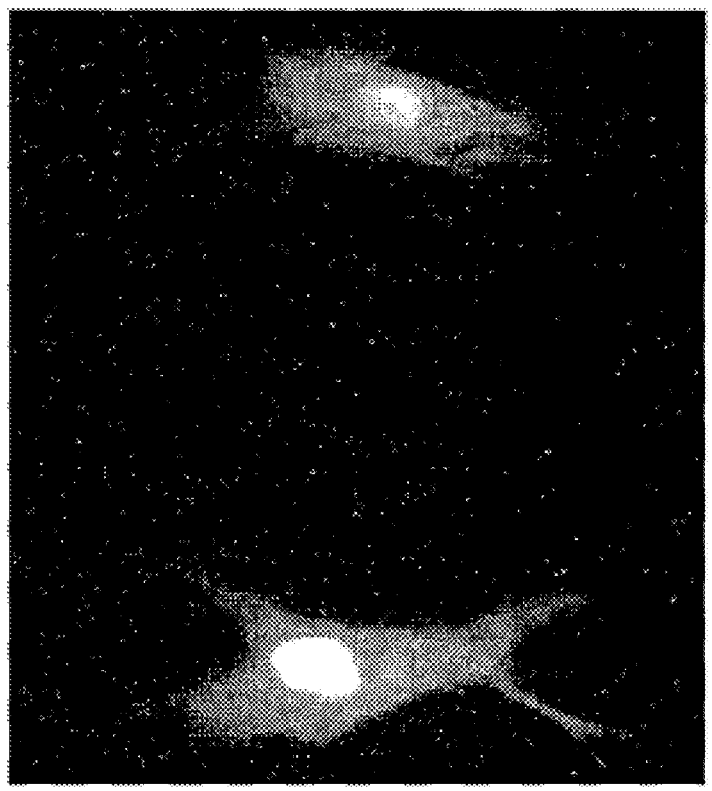
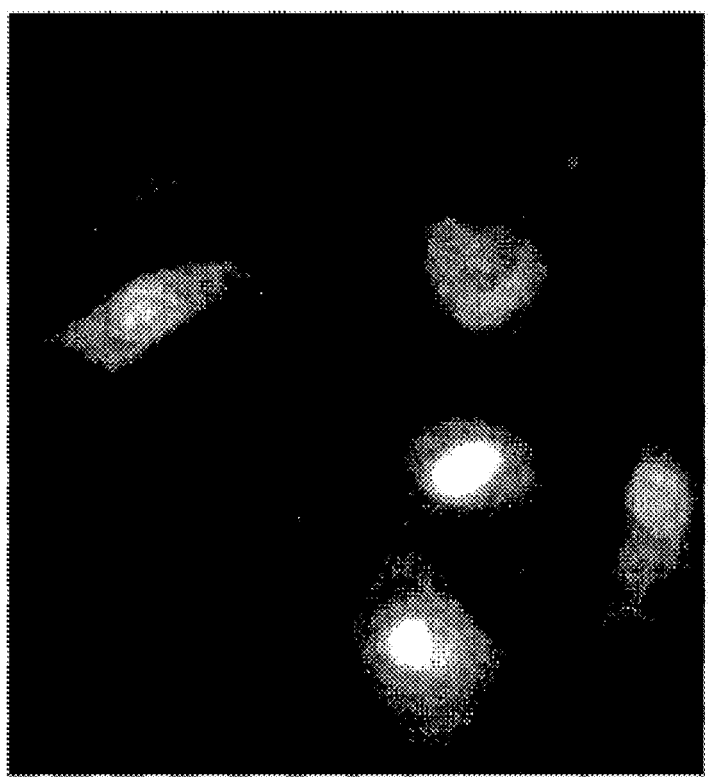
FIGURE 14

FIGURE 19
A
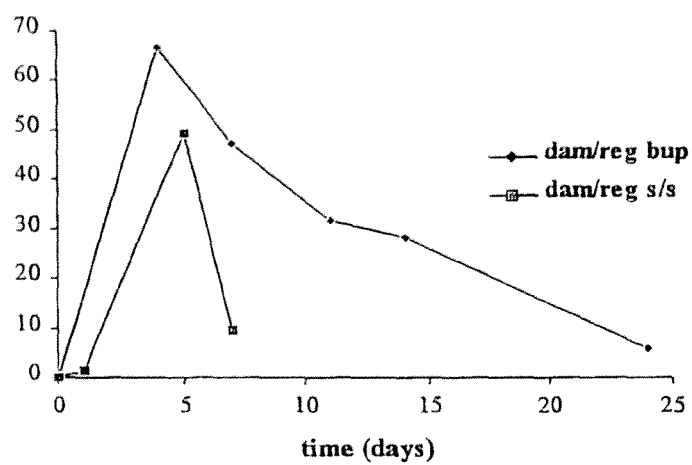
B
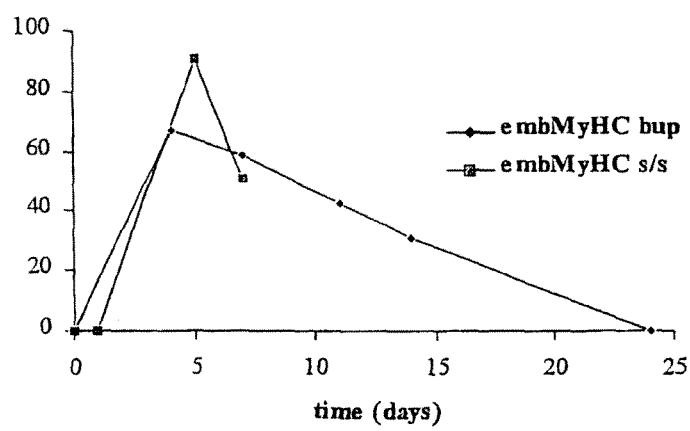

FIGURE 20
A
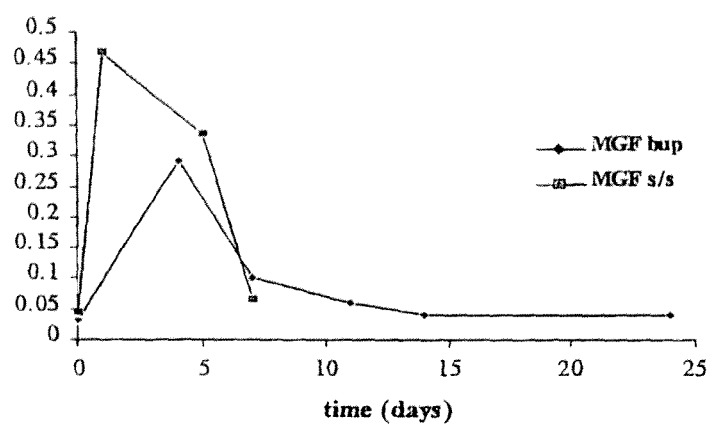
B
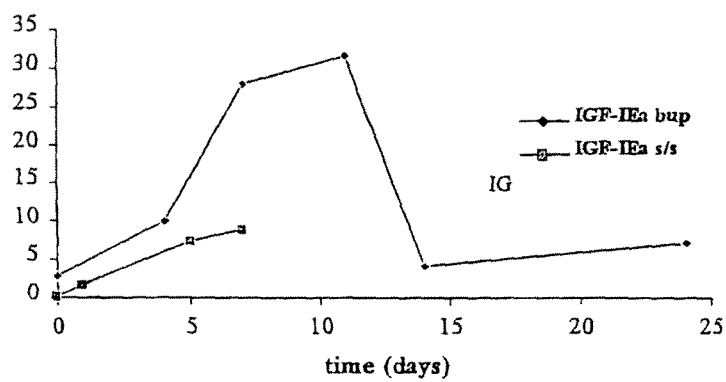

SEQUENCE LISTING

<160> NUMBER OF SEQ ID NOS: 26

<210> SEQ ID NO 1
<211> LENGTH: 517
<212> TYPE: DNA
<213> ORGANISM: Homo sapiens
<220> FEATURE:
<221> NAME/KEY: CDS
<222> LOCATION: (1)..(330)
<220> FEATURE:
<221> NAME/KEY: misc_feature
<222> LOCATION: (327)..(327)
<223> OTHER INFORMATION: n is a, c, g, or t

<400> SEQUENCE: 1

| | | | | | | | | | | | | | | | | |
|---|---|---|---|---|---|---|---|---|---|---|---|---|---|---|---|---|
| gga | ccg | gag | acg | ctc | tgc | ggg | gct | gag | ctg | gtg | gat | gct | ctt | cag | ttc | 48 |
| Gly | Pro | Glu | Thr | Leu | Cys | Gly | Ala | Glu | Leu | Val | Asp | Ala | Leu | Gln | Phe | |
| 1 | | | | 5 | | | | | 10 | | | | | 15 | | |
| gtg | tgt | gga | gac | agg | ggc | ttt | tat | ttc | aac | aag | ccc | aca | ggg | tat | ggc | 96 |
| Val | Cys | Gly | Asp | Arg | Gly | Phe | Tyr | Phe | Asn | Lys | Pro | Thr | Gly | Tyr | Gly | |
| | | | 20 | | | | | 25 | | | | | 30 | | | |
| tcc | agc | agt | cgg | agg | gcg | cct | cag | aca | ggc | atc | gtg | gat | gag | tgc | tgc | 144 |
| Ser | Ser | Ser | Arg | Arg | Ala | Pro | Gln | Thr | Gly | Ile | Val | Asp | Glu | Cys | Cys | |
| | | 35 | | | | | 40 | | | | | 45 | | | | |
| ttc | cgg | agc | tgt | gat | cta | agg | agg | ctg | gag | atg | tat | tgc | gca | ccc | ctc | 192 |
| Phe | Arg | Ser | Cys | Asp | Leu | Arg | Arg | Leu | Glu | Met | Tyr | Cys | Ala | Pro | Leu | |
| | 50 | | | | | 55 | | | | | 60 | | | | | |
| aag | cct | gcc | aag | tca | gct | cgc | tct | gtc | cgt | gcc | cag | cgc | cac | acc | gac | 240 |
| Lys | Pro | Ala | Lys | Ser | Ala | Arg | Ser | Val | Arg | Ala | Gln | Arg | His | Thr | Asp | |
| 65 | | | | | 70 | | | | | 75 | | | | | 80 | |
| atg | ccc | aag | acc | cag | aag | tat | cag | ccc | cca | tct | acc | aac | aag | aac | acg | 288 |
| Met | Pro | Lys | Thr | Gln | Lys | Tyr | Gln | Pro | Pro | Ser | Thr | Asn | Lys | Asn | Thr | |
| | | | 85 | | | | | 90 | | | | | 95 | | | |
| aag | tct | cag | aga | agg | aaa | gga | agt | aca | ttt | gaa | gaa | cgn | aag | | | 330 |
| Lys | Ser | Gln | Arg | Arg | Lys | Gly | Ser | Thr | Phe | Glu | Glu | Arg | Lys | | | |
| | | | 100 | | | | | 105 | | | | | 110 | | | | tagagggagt gcaggaaaca agaactacag gatgtagaag acccttctga ggagtgaaga    390 aggacaggcc accgcaggac cctttgctct gcacagttac ctgtaaacat tggaataccg    450 gccaaaaaat aagtttgatc acatttcaaa gatggcattt cccccaatga aatacacaag    510 taaacat    517

<210> SEQ ID NO 2
<211> LENGTH: 110
<212> TYPE: PRT
<213> ORGANISM: Homo sapiens

<400> SEQUENCE: 2

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
        50                  55                  60

Lys Pro Ala Lys Ser Ala Arg Ser Val Arg Ala Gln Arg His Thr Asp
65                  70                  75                  80

Met Pro Lys Thr Gln Lys Tyr Gln Pro Pro Ser Thr Asn Lys Asn Thr
                85                  90                  95

```
Lys Ser Gln Arg Arg Lys Gly Ser Thr Phe Glu Glu Arg Lys
            100                 105                 110
```

<210> SEQ ID NO 3
<211> LENGTH: 539
<212> TYPE: DNA
<213> ORGANISM: Rattus norvegicus
<220> FEATURE:
<221> NAME/KEY: CDS
<222> LOCATION: (1)..(333)

<400> SEQUENCE: 3

```
gga cca gag acc ctt tgc ggg gct gag ctg gtg gac gct ctt cag ttc      48
Gly Pro Glu Thr Leu Cys Gly Ala Glu Leu Val Asp Ala Leu Gln Phe
1               5                   10                  15 gtg tgt gga cca agg ggc ttt tac ttc aac aag ccc aca gtc tat ggc      96
Val Cys Gly Pro Arg Gly Phe Tyr Phe Asn Lys Pro Thr Val Tyr Gly
            20                  25                  30 tcc agc att cgg agg gca cca cag acg ggc att gtg gat gag tgt tgc     144
Ser Ser Ile Arg Arg Ala Pro Gln Thr Gly Ile Val Asp Glu Cys Cys
        35                  40                  45 ttc cgg agc tgt gat ctg agg agg ctg gag atg tac tgt gtc cgc tgc     192
Phe Arg Ser Cys Asp Leu Arg Arg Leu Glu Met Tyr Cys Val Arg Cys
    50                  55                  60 aag cct aca aag tca gct cgt tcc atc cgg gcc cag cgc cac act gac     240
Lys Pro Thr Lys Ser Ala Arg Ser Ile Arg Ala Gln Arg His Thr Asp
65                  70                  75                  80 atg ccc aag act cag aag tcc cag ccc cta tcg aca cac aag aaa agg     288
Met Pro Lys Thr Gln Lys Ser Gln Pro Leu Ser Thr His Lys Lys Arg
                85                  90                  95 aag ctg caa agg aga agg aaa gga agt aca ctt gaa gaa cac aag         333
Lys Leu Gln Arg Arg Arg Lys Gly Ser Thr Leu Glu Glu His Lys
            100                 105                 110 tagaggaagt gcaggaaaca agacctacag aatgtaggag gagcctcccg aggaacagaa   393
aatgccacgt caccgcaaga tcctttgctg cttgagcaac ctgcaaaaca tcggaacacc   453
tgccaaatat caataatgag ttcaatatca tttcagagat gggcatttcc ctcaatgaaa   513
tacacaagta acattcccg gaattc                                         539
```

<210> SEQ ID NO 4
<211> LENGTH: 111
<212> TYPE: PRT
<213> ORGANISM: Rattus norvegicus

<400> SEQUENCE: 4

```
Gly Pro Glu Thr Leu Cys Gly Ala Glu Leu Val Asp Ala Leu Gln Phe
1               5                   10                  15

Val Cys Gly Pro Arg Gly Phe Tyr Phe Asn Lys Pro Thr Val Tyr Gly
            20                  25                  30

Ser Ser Ile Arg Arg Ala Pro Gln Thr Gly Ile Val Asp Glu Cys Cys
        35                  40                  45

Phe Arg Ser Cys Asp Leu Arg Arg Leu Glu Met Tyr Cys Val Arg Cys
    50                  55                  60

Lys Pro Thr Lys Ser Ala Arg Ser Ile Arg Ala Gln Arg His Thr Asp
65                  70                  75                  80

Met Pro Lys Thr Gln Lys Ser Gln Pro Leu Ser Thr His Lys Lys Arg
                85                  90                  95

Lys Leu Gln Arg Arg Arg Lys Gly Ser Thr Leu Glu Glu His Lys
            100                 105                 110
```

<210> SEQ ID NO 5
<211> LENGTH: 523
<212> TYPE: DNA
<213> ORGANISM: Oryctolagus cuniculus
<220> FEATURE:
<221> NAME/KEY: CDS
<222> LOCATION: (1)..(333)

<400> SEQUENCE: 5

```
gga ccg gag acg ctc tgc ggt gct gag ctg gtg gat gct ctt cag ttc      48
Gly Pro Glu Thr Leu Cys Gly Ala Glu Leu Val Asp Ala Leu Gln Phe
1               5                   10                  15 gtg tgt gga gac agg ggc ttt tat ttc aac aag ccc aca gga tac ggc      96
Val Cys Gly Asp Arg Gly Phe Tyr Phe Asn Lys Pro Thr Gly Tyr Gly
                20                  25                  30 tcc agc agt cgg agg gca cct cag aca ggc atc gtg gat gag tgc tgc     144
Ser Ser Ser Arg Arg Ala Pro Gln Thr Gly Ile Val Asp Glu Cys Cys
            35                  40                  45 ttc cgg agc tgt gat ctg agg agg ctg gag atg tac tgt gca ccc ctc     192
Phe Arg Ser Cys Asp Leu Arg Arg Leu Glu Met Tyr Cys Ala Pro Leu
        50                  55                  60 aag ccg gca aag gca gcc cgc tcc gtc cgt gcc cag cgc cac acc gac     240
Lys Pro Ala Lys Ala Ala Arg Ser Val Arg Ala Gln Arg His Thr Asp
65                  70                  75                  80 atg ccc aag act cag aag tat cag cct cca tct acc aac aag aaa atg     288
Met Pro Lys Thr Gln Lys Tyr Gln Pro Pro Ser Thr Asn Lys Lys Met
                85                  90                  95 aag tct cag agg aga agg aaa gga agt aca ttt gaa gaa cac aag          333
Lys Ser Gln Arg Arg Arg Lys Gly Ser Thr Phe Glu Glu His Lys
            100                 105                 110 tagagggagt gcaggaaaca agaactacag gatgtaggaa gacccttctg aggagtgaag    393
aaggacaggc caccgcagga ccctttgctc tgcacagtta cctgtaaaca ttggaatacc    453
ggccaaaaaa taagtttgat cacatttcaa agatggcatt tcccccaatg aaatacacaa    513
gtaaacattc                                                           523
```

<210> SEQ ID NO 6
<211> LENGTH: 111
<212> TYPE: PRT
<213> ORGANISM: Oryctolagus cuniculus

<400> SEQUENCE: 6

```
Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
        50                  55                  60

Lys Pro Ala Lys Ala Ala Arg Ser Val Arg Ala Gln Arg His Thr Asp
65                  70                  75                  80

Met Pro Lys Thr Gln Lys Tyr Gln Pro Pro Ser Thr Asn Lys Lys Met
                85                  90                  95

Lys Ser Gln Arg Arg Arg Lys Gly Ser Thr Phe Glu Glu His Lys
            100                 105                 110
```

<210> SEQ ID NO 7
<211> LENGTH: 10

```
<212> TYPE: DNA
<213> ORGANISM: Artificial Sequence
<220> FEATURE:
<223> OTHER INFORMATION: Translation initiation sequence

<400> SEQUENCE: 7
gccaccatgg                                                                  10

<210> SEQ ID NO 8
<211> LENGTH: 10
<212> TYPE: DNA
<213> ORGANISM: Artificial Sequence
<220> FEATURE:
<223> OTHER INFORMATION: Translation initiation sequence

<400> SEQUENCE: 8
gcccccatgg                                                                  10

<210> SEQ ID NO 9
<211> LENGTH: 317
<212> TYPE: DNA
<213> ORGANISM: Homo sapiens
<220> FEATURE:
<221> NAME/KEY: CDS
<222> LOCATION: (1)..(315)

<400> SEQUENCE: 9 gga ccg gag acg ctc tgc ggg gct gag ctg gtg gat gct ctt cag ttc            48
Gly Pro Glu Thr Leu Cys Gly Ala Glu Leu Val Asp Ala Leu Gln Phe
1               5                   10                  15 gtg tgt gga gac agg ggc ttt tat ttc aac aag ccc aca ggg tat ggc            96
Val Cys Gly Asp Arg Gly Phe Tyr Phe Asn Lys Pro Thr Gly Tyr Gly
            20                  25                  30 tcc agc agt cgg agg gcg cct cag aca ggc atc gtg gat gag tgc tgc           144
Ser Ser Ser Arg Arg Ala Pro Gln Thr Gly Ile Val Asp Glu Cys Cys
        35                  40                  45 ttc cgg agc tgt gat cta agg agg ctg gag atg tat tgc gca ccc ctc           192
Phe Arg Ser Cys Asp Leu Arg Arg Leu Glu Met Tyr Cys Ala Pro Leu
    50                  55                  60 aag cct gcc aag tca gct cgc tct gtc cgt gcc cag cgc cac acc gac           240
Lys Pro Ala Lys Ser Ala Arg Ser Val Arg Ala Gln Arg His Thr Asp
65                  70                  75                  80 atg ccc aag acc cag aag gaa gta cat ttg aag aac gca agt aga ggg           288
Met Pro Lys Thr Gln Lys Glu Val His Leu Lys Asn Ala Ser Arg Gly
                85                  90                  95 agt gca gga aac aag aac tac agg atg ag                                    317
Ser Ala Gly Asn Lys Asn Tyr Arg Met
                100                 105

<210> SEQ ID NO 10
<211> LENGTH: 105
<212> TYPE: PRT
<213> ORGANISM: Homo sapiens

<400> SEQUENCE: 10

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60
```

Lys Pro Ala Lys Ser Arg Ser Val Arg Ala Gln Arg His Thr Asp
65                  70                  75                  80

Met Pro Lys Thr Gln Lys Glu Val His Leu Lys Asn Ala Ser Arg Gly
                85                  90                  95

Ser Ala Gly Asn Lys Asn Tyr Arg Met
            100                 105

<210> SEQ ID NO 11
<211> LENGTH: 487
<212> TYPE: DNA
<213> ORGANISM: Rattus norvegicus
<220> FEATURE:
<221> NAME/KEY: CDS
<222> LOCATION: (1)..(315)

<400> SEQUENCE: 11 gga cca gag acc ctt tgc ggg gct gag ctg gtg gac gct ctt cag ttc      48
Gly Pro Glu Thr Leu Cys Gly Ala Glu Leu Val Asp Ala Leu Gln Phe
1               5                   10                  15 gtg tgt gga cca agg ggc ttt tac ttc aac aag ccc aca gtc tat ggc      96
Val Cys Gly Pro Arg Gly Phe Tyr Phe Asn Lys Pro Thr Val Tyr Gly
                20                  25                  30 tcc agc att cgg agg gca cca cag acg ggc att gtg gat gag tgt tgc     144
Ser Ser Ile Arg Arg Ala Pro Gln Thr Gly Ile Val Asp Glu Cys Cys
            35                  40                  45 ttc cgg agc tgt gat ctg agg agg ctg gag atg tac tgt gtc cgc tgc     192
Phe Arg Ser Cys Asp Leu Arg Arg Leu Glu Met Tyr Cys Val Arg Cys
        50                  55                  60 aag cct aca aag tca gct cgt tcc atc cgg gcc cag cgc cac act gac     240
Lys Pro Thr Lys Ser Ala Arg Ser Ile Arg Ala Gln Arg His Thr Asp
65                  70                  75                  80 atg ccc aag act cag aag gaa gta cac ttg aag aac aca agt aga gga     288
Met Pro Lys Thr Gln Lys Glu Val His Leu Lys Asn Thr Ser Arg Gly
                85                  90                  95 agt gca gga aac aag acc tac aga atg taggaggagc ctcccgagga           335
Ser Ala Gly Asn Lys Thr Tyr Arg Met
            100                 105 acagaaaatg ccacgtcacc gcaagatcct tgctgcttg agcaacctgc aaaacatcgg    395
aacacctgcc aaatatcaat aatgagttca atatcatttc agagatgggc atttccctca   455
atgaaataca caagtaaaca ttcccggaat tc                                 487

<210> SEQ ID NO 12
<211> LENGTH: 105
<212> TYPE: PRT
<213> ORGANISM: Rattus norvegicus

<400> SEQUENCE: 12

Gly Pro Glu Thr Leu Cys Gly Ala Glu Leu Val Asp Ala Leu Gln Phe
1               5                   10                  15

Val Cys Gly Pro Arg Gly Phe Tyr Phe Asn Lys Pro Thr Val Tyr Gly
                20                  25                  30

Ser Ser Ile Arg Arg Ala Pro Gln Thr Gly Ile Val Asp Glu Cys Cys
            35                  40                  45

Phe Arg Ser Cys Asp Leu Arg Arg Leu Glu Met Tyr Cys Val Arg Cys
        50                  55                  60

Lys Pro Thr Lys Ser Ala Arg Ser Ile Arg Ala Gln Arg His Thr Asp
65                  70                  75                  80

Met Pro Lys Thr Gln Lys Glu Val His Leu Lys Asn Thr Ser Arg Gly

```
                    85                  90                  95
Ser Ala Gly Asn Lys Thr Tyr Arg Met
            100                 105

<210> SEQ ID NO 13
<211> LENGTH: 471
<212> TYPE: DNA
<213> ORGANISM: Oryctolagus cuniculus
<220> FEATURE:
<221> NAME/KEY: CDS
<222> LOCATION: (1)..(315)

<400> SEQUENCE: 13 gga ccg gag acg ctc tgc ggt gct gag ctg gtg gat gct ctt cag ttc        48
Gly Pro Glu Thr Leu Cys Gly Ala Glu Leu Val Asp Ala Leu Gln Phe
1               5                   10                  15 gtg tgt gga gac agg ggc ttt tat ttc aac aag ccc aca gga tac ggc        96
Val Cys Gly Asp Arg Gly Phe Tyr Phe Asn Lys Pro Thr Gly Tyr Gly
            20                  25                  30 tcc agc agt cgg agg gca cct cag aca ggc atc gtg gat gag tgc tgc       144
Ser Ser Ser Arg Arg Ala Pro Gln Thr Gly Ile Val Asp Glu Cys Cys
        35                  40                  45 ttc cgg agc tgt gat ctg agg agg ctg gag atg tac tgt gca ccc ctc       192
Phe Arg Ser Cys Asp Leu Arg Arg Leu Glu Met Tyr Cys Ala Pro Leu
    50                  55                  60 aag ccg gca aag gca gcc cgc tcc gtc cgt gcc cag cgc cac acc gac       240
Lys Pro Ala Lys Ala Ala Arg Ser Val Arg Ala Gln Arg His Thr Asp
65                  70                  75                  80 atg ccc aag act cag aag gaa gta cat ttg aag aac aca agt aga ggg       288
Met Pro Lys Thr Gln Lys Glu Val His Leu Lys Asn Thr Ser Arg Gly
                85                  90                  95 agt gca gga aac aag aac tac agg atg taggaagacc cttctgagga             335
Ser Ala Gly Asn Lys Asn Tyr Arg Met
            100                 105 gtgaagaagg acaggccacc gcaggaccct tgctctgca cagttacctg taaacattgg       395
aataccggcc aaaaaataag tttgatcaca tttcaaagat ggcatttccc ccaatgaaat      455
acacaagtaa acattc                                                      471

<210> SEQ ID NO 14
<211> LENGTH: 105
<212> TYPE: PRT
<213> ORGANISM: Oryctolagus cuniculus

<400> SEQUENCE: 14

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Ala Lys Ala Ala Arg Ser Val Arg Ala Gln Arg His Thr Asp
65                  70                  75                  80

Met Pro Lys Thr Gln Lys Glu Val His Leu Lys Asn Thr Ser Arg Gly
                85                  90                  95

Ser Ala Gly Asn Lys Asn Tyr Arg Met
            100                 105
```

```
<210> SEQ ID NO 15
<211> LENGTH: 517
<212> TYPE: DNA
<213> ORGANISM: Homo sapiens
<220> FEATURE:
<221> NAME/KEY: CDS
<222> LOCATION: (1)..(333)

<400> SEQUENCE: 15 gga ccg gag acg ctc tgc ggg gct gag ctg gtg gat gct ctt cag ttc      48
Gly Pro Glu Thr Leu Cys Gly Ala Glu Leu Val Asp Ala Leu Gln Phe
1               5                   10                  15 gtg tgt gga gac agg ggc ttt tat ttc aac aag ccc aca ggg tat ggc      96
Val Cys Gly Asp Arg Gly Phe Tyr Phe Asn Lys Pro Thr Gly Tyr Gly
            20                  25                  30 tcc agc agt cgg agg gcg cct cag aca ggc atc gtg gat gag tgc tgc     144
Ser Ser Ser Arg Arg Ala Pro Gln Thr Gly Ile Val Asp Glu Cys Cys
        35                  40                  45 ttc cgg agc tgt gat cta agg agg ctg gag atg tat tgc gca ccc ctc     192
Phe Arg Ser Cys Asp Leu Arg Arg Leu Glu Met Tyr Cys Ala Pro Leu
    50                  55                  60 aag cct gcc aag tca gct cgc tct gtc cgt gcc cag cgc cac acc gac     240
Lys Pro Ala Lys Ser Ala Arg Ser Val Arg Ala Gln Arg His Thr Asp
65                  70                  75                  80 atg ccc aag acc cag aag tat cag ccc cca tct acc aac aag aac acg     288
Met Pro Lys Thr Gln Lys Tyr Gln Pro Pro Ser Thr Asn Lys Asn Thr
                85                  90                  95 aag tct cag aga agg aaa gga agt aca ttt gaa gaa cac aag tag         333
Lys Ser Gln Arg Arg Lys Gly Ser Thr Phe Glu Glu His Lys
            100                 105                 110 agggagtgca ggaaacaaga actacaggat gtagaagacc cttctgagga gtgaagaagg    393
acaggccacc gcaggaccct tgctctgca  cagttagtac ctaacattgg aataccggcc    453
aaaaaataag tttgatcaca tttcaaagat ggcatttccc ccaatgaaat acacaagtaa    513
acat                                                                517

<210> SEQ ID NO 16
<211> LENGTH: 110
<212> TYPE: PRT
<213> ORGANISM: Homo sapiens

<400> SEQUENCE: 16

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Ala Lys Ser Ala Arg Ser Val Arg Ala Gln Arg His Thr Asp
65                  70                  75                  80

Met Pro Lys Thr Gln Lys Tyr Gln Pro Pro Ser Thr Asn Lys Asn Thr
                85                  90                  95

Lys Ser Gln Arg Arg Lys Gly Ser Thr Phe Glu Glu His Lys
            100                 105                 110

<210> SEQ ID NO 17
<211> LENGTH: 538
```

<212> TYPE: DNA
<213> ORGANISM: Rattus norvegicus
<220> FEATURE:
<221> NAME/KEY: CDS
<222> LOCATION: (1)..(333)

<400> SEQUENCE: 17

```
gga cca gag acc ctt tgc ggg gct gag ctg gtg gac gct ctt cag ttc      48
Gly Pro Glu Thr Leu Cys Gly Ala Glu Leu Val Asp Ala Leu Gln Phe
1               5                   10                  15 gtg tgt gga cca agg ggc ttt tac ttc aac aag ccc aca gtc tat ggc      96
Val Cys Gly Pro Arg Gly Phe Tyr Phe Asn Lys Pro Thr Val Tyr Gly
            20                  25                  30 tcc agc att cgg agg gca cca cag acg ggc att gtg gat gag tgt tgc     144
Ser Ser Ile Arg Arg Ala Pro Gln Thr Gly Ile Val Asp Glu Cys Cys
        35                  40                  45 ttc cgg agc tgt gat ctg agg agg ctg gag atg tac tgt gtc cgc tgc     192
Phe Arg Ser Cys Asp Leu Arg Arg Leu Glu Met Tyr Cys Val Arg Cys
    50                  55                  60 aag cct aca aag tca gct cgt tcc atc cgg gcc cag cgc cac act gac     240
Lys Pro Thr Lys Ser Ala Arg Ser Ile Arg Ala Gln Arg His Thr Asp
65                  70                  75                  80 atg ccc aag act cag aag tcc cag ccc cta tcg aca cac aag aaa agg     288
Met Pro Lys Thr Gln Lys Ser Gln Pro Leu Ser Thr His Lys Lys Arg
                85                  90                  95 aag ctg caa agg aga agg aaa gga agt aca ctt gaa gaa cac aag          333
Lys Leu Gln Arg Arg Arg Lys Gly Ser Thr Leu Glu Glu His Lys
            100                 105                 110 tagaggaagt gcaggaaaca agacctacag aatgtaggag gagcctcccg aggaacagaa    393
aatgccacgt caccgcaaga tcctttgctg cttggcaacc tgcaaaacat cggaacacct    453
gccaaatatc aataatgagt tcaatatcat ttcagagatg ggcatttccc tcaatgaaat    513
acacaagtaa acattcccgg aattc                                          538
```

<210> SEQ ID NO 18
<211> LENGTH: 111
<212> TYPE: PRT
<213> ORGANISM: Rattus norvegicus

<400> SEQUENCE: 18

```
Gly Pro Glu Thr Leu Cys Gly Ala Glu Leu Val Asp Ala Leu Gln Phe
1               5                   10                  15

Val Cys Gly Pro Arg Gly Phe Tyr Phe Asn Lys Pro Thr Val Tyr Gly
            20                  25                  30

Ser Ser Ile Arg Arg Ala Pro Gln Thr Gly Ile Val Asp Glu Cys Cys
        35                  40                  45

Phe Arg Ser Cys Asp Leu Arg Arg Leu Glu Met Tyr Cys Val Arg Cys
    50                  55                  60

Lys Pro Thr Lys Ser Ala Arg Ser Ile Arg Ala Gln Arg His Thr Asp
65                  70                  75                  80

Met Pro Lys Thr Gln Lys Ser Gln Pro Leu Ser Thr His Lys Lys Arg
                85                  90                  95

Lys Leu Gln Arg Arg Arg Lys Gly Ser Thr Leu Glu Glu His Lys
            100                 105                 110
```

<210> SEQ ID NO 19
<211> LENGTH: 523
<212> TYPE: DNA
<213> ORGANISM: Oryctolagus cuniculus
<220> FEATURE:

```
<221> NAME/KEY: CDS
<222> LOCATION: (1)..(333)

<400> SEQUENCE: 19 gga ccg gag acg ctc tgc ggt gct gag ctg gtg gat gct ctt cag ttc      48
Gly Pro Glu Thr Leu Cys Gly Ala Glu Leu Val Asp Ala Leu Gln Phe
1               5                   10                  15 gtg tgt gga gac agg ggc ttt tat ttc aac aag ccc aca gga tac ggc      96
Val Cys Gly Asp Arg Gly Phe Tyr Phe Asn Lys Pro Thr Gly Tyr Gly
            20                  25                  30 tcc agc agt cgg agg gca cct cag aca ggc atc gtg gat gag tgc tgc     144
Ser Ser Ser Arg Arg Ala Pro Gln Thr Gly Ile Val Asp Glu Cys Cys
        35                  40                  45 ttc cgg agc tgt gat ctg agg agg ctg gag atg tac tgt gca ccc ctc     192
Phe Arg Ser Cys Asp Leu Arg Arg Leu Glu Met Tyr Cys Ala Pro Leu
    50                  55                  60 aag ccg gca aag gca gcc cgc tcc gtc cgt gcc cag cgc cac acc gac     240
Lys Pro Ala Lys Ala Ala Arg Ser Val Arg Ala Gln Arg His Thr Asp
65                  70                  75                  80 atg ccc aag act cag aag tat cag cct cca tct acc aac aag aaa atg     288
Met Pro Lys Thr Gln Lys Tyr Gln Pro Pro Ser Thr Asn Lys Lys Met
                85                  90                  95 aag tct cag agg aga agg aaa gga agt aca ttt gaa gaa cac aag          333
Lys Ser Gln Arg Arg Arg Lys Gly Ser Thr Phe Glu Glu His Lys
            100                 105                 110 tagagggagt gcaggaaaca agaactacag gatgtaggaa gacccttctg aggagtgaag     393
aaggacaggc caccgcagga ccctttgctc tgcacagtta cctgtaaaca ttggaatacc     453
ggccaaaaaa taagtttgat cacatttcaa agatggcatt tcccccaatg aaatacacaa     513
gtaaacattc                                                            523

<210> SEQ ID NO 20
<211> LENGTH: 111
<212> TYPE: PRT
<213> ORGANISM: Oryctolagus cuniculus

<400> SEQUENCE: 20

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

Ser Ser Ser Arg Arg Ala Pro Gln Thr Gly Ile Val Asp Glu Cys Cys
        35                  40                  45

Phe Arg Ser Cys Asp Leu Arg Arg Leu Glu Met Tyr Cys Ala Pro Leu
    50                  55                  60

Lys Pro Ala Lys Ala Ala Arg Ser Val Arg Ala Gln Arg His Thr Asp
65                  70                  75                  80

Met Pro Lys Thr Gln Lys Tyr Gln Pro Pro Ser Thr Asn Lys Lys Met
                85                  90                  95

Lys Ser Gln Arg Arg Arg Lys Gly Ser Thr Phe Glu Glu His Lys
            100                 105                 110

<210> SEQ ID NO 21
<211> LENGTH: 318
<212> TYPE: DNA
<213> ORGANISM: Homo sapiens
<220> FEATURE:
<221> NAME/KEY: CDS
<222> LOCATION: (1)..(318)
```

<400> SEQUENCE: 21

```
gga ccg gag acg ctc tgc ggg gct gag ctg gtg gat gct ctt cag ttc      48
Gly Pro Glu Thr Leu Cys Gly Ala Glu Leu Val Asp Ala Leu Gln Phe
  1               5                  10                  15 gtg tgt gga gac agg ggc ttt tat ttc aac aag ccc aca ggg tat ggc      96
Val Cys Gly Asp Arg Gly Phe Tyr Phe Asn Lys Pro Thr Gly Tyr Gly
             20                  25                  30 tcc agc agt cgg agg gcg cct cag aca ggc atc gtg gat gag tgc tgc     144
Ser Ser Ser Arg Arg Ala Pro Gln Thr Gly Ile Val Asp Glu Cys Cys
         35                  40                  45 ttc cgg agc tgt gat cta agg agg ctg gag atg tat tgc gca ccc ctc     192
Phe Arg Ser Cys Asp Leu Arg Arg Leu Glu Met Tyr Cys Ala Pro Leu
     50                  55                  60 aag cct gcc aag tca gct cgc tct gtc cgt gcc cag cgc cac acc gac     240
Lys Pro Ala Lys Ser Ala Arg Ser Val Arg Ala Gln Arg His Thr Asp
 65                  70                  75                  80 atg ccc aag acc cag aag gaa gta cat ttg aag aac gca agt aga ggg     288
Met Pro Lys Thr Gln Lys Glu Val His Leu Lys Asn Ala Ser Arg Gly
                 85                  90                  95 agt gca gga aac aag aac tac agg atg tag                             318
Ser Ala Gly Asn Lys Asn Tyr Arg Met
                100                 105

<210> SEQ ID NO 22
<211> LENGTH: 105
<212> TYPE: PRT
<213> ORGANISM: Homo sapiens

<400> SEQUENCE: 22

Gly Pro Glu Thr Leu Cys Gly Ala Glu Leu Val Asp Ala Leu Gln Phe
  1               5                  10                  15

Val Cys Gly Asp Arg Gly Phe Tyr Phe Asn Lys Pro Thr Gly Tyr Gly
             20                  25                  30

Ser Ser Ser Arg Arg Ala Pro Gln Thr Gly Ile Val Asp Glu Cys Cys
         35                  40                  45

Phe Arg Ser Cys Asp Leu Arg Arg Leu Glu Met Tyr Cys Ala Pro Leu
     50                  55                  60

Lys Pro Ala Lys Ser Ala Arg Ser Val Arg Ala Gln Arg His Thr Asp
 65                  70                  75                  80

Met Pro Lys Thr Gln Lys Glu Val His Leu Lys Asn Ala Ser Arg Gly
                 85                  90                  95

Ser Ala Gly Asn Lys Asn Tyr Arg Met
                100                 105

<210> SEQ ID NO 23
<211> LENGTH: 487
<212> TYPE: DNA
<213> ORGANISM: Rattus norvegicus
<220> FEATURE:
<221> NAME/KEY: CDS
<222> LOCATION: (1)..(315)

<400> SEQUENCE: 23 gga cca gag acc ctt tgc ggg gct gag ctg gtg gac gct ctt cag ttc      48
Gly Pro Glu Thr Leu Cys Gly Ala Glu Leu Val Asp Ala Leu Gln Phe
  1               5                  10                  15 gtg tgt gga cca agg ggc ttt tac ttc aac aag ccc aca gtc tat ggc      96
Val Cys Gly Pro Arg Gly Phe Tyr Phe Asn Lys Pro Thr Val Tyr Gly
             20                  25                  30 tcc agc att cgg agg gca cca cag acg ggc att gtg gat gag tgt tgc     144
```

```
Ser Ser Ile Arg Arg Ala Pro Gln Thr Gly Ile Val Asp Glu Cys Cys
        35                  40                  45 ttc cgg agc tgt gat ctg agg agg ctg gag atg tac tgt gtc cgc tgc    192
Phe Arg Ser Cys Asp Leu Arg Arg Leu Glu Met Tyr Cys Val Arg Cys
 50                  55                  60 aag cct aca aag tca gct cgt tcc atc cgg gcc cag cgc cac act gac    240
Lys Pro Thr Lys Ser Ala Arg Ser Ile Arg Ala Gln Arg His Thr Asp
 65                  70                  75                  80 atg ccc aag act cag aag gaa gta cac ttg aag aac aca agt aga gga    288
Met Pro Lys Thr Gln Lys Glu Val His Leu Lys Asn Thr Ser Arg Gly
                 85                  90                  95 agt gca gga aac aag acc tac aga atg taggaggagc ctcccgagga          335
Ser Ala Gly Asn Lys Thr Tyr Arg Met
                100                 105 acagaaaatg ccacgtcacc gcaagatcct tgctgcttg agcaacctgc aaaacatcgg    395
aacacctgcc aaatatcaat aatgagttca atatcatttc agagatgggc atttccctca   455
atgaaataca caagtaaaca ttcccggaat tc                                 487

<210> SEQ ID NO 24
<211> LENGTH: 105
<212> TYPE: PRT
<213> ORGANISM: Rattus norvegicus

<400> SEQUENCE: 24

Gly Pro Glu Thr Leu Cys Gly Ala Glu Leu Val Asp Ala Leu Gln Phe
 1               5                  10                  15

Val Cys Gly Pro Arg Gly Phe Tyr Phe Asn Lys Pro Thr Val Tyr Gly
                20                  25                  30

Ser Ser Ile Arg Arg Ala Pro Gln Thr Gly Ile Val Asp Glu Cys Cys
        35                  40                  45

Phe Arg Ser Cys Asp Leu Arg Arg Leu Glu Met Tyr Cys Val Arg Cys
 50                  55                  60

Lys Pro Thr Lys Ser Ala Arg Ser Ile Arg Ala Gln Arg His Thr Asp
 65                  70                  75                  80

Met Pro Lys Thr Gln Lys Glu Val His Leu Lys Asn Thr Ser Arg Gly
                 85                  90                  95

Ser Ala Gly Asn Lys Thr Tyr Arg Met
                100                 105

<210> SEQ ID NO 25
<211> LENGTH: 471
<212> TYPE: DNA
<213> ORGANISM: Oryctolagus cuniculus
<220> FEATURE:
<221> NAME/KEY: CDS
<222> LOCATION: (1)..(315)

<400> SEQUENCE: 25 gga ccg gag acg ctc tgc ggt gct gag ctg gtg gat gct ctt cag ttc    48
Gly Pro Glu Thr Leu Cys Gly Ala Glu Leu Val Asp Ala Leu Gln Phe
 1               5                  10                  15 gtg tgt gga gac agg ggc ttt tat ttc aac aag ccc aca gga tac ggc    96
Val Cys Gly Asp Arg Gly Phe Tyr Phe Asn Lys Pro Thr Gly Tyr Gly
                20                  25                  30 tcc agc agt cgg agg gca cct cag aca ggc atc gtg gat gag tgc tgc   144
Ser Ser Ser Arg Arg Ala Pro Gln Thr Gly Ile Val Asp Glu Cys Cys
        35                  40                  45 ttc cgg agc tgt gat ctg agg agg ctg gag atg tac tgt gca ccc ctc   192
Phe Arg Ser Cys Asp Leu Arg Arg Leu Glu Met Tyr Cys Ala Pro Leu
 50                  55                  60
```

```
                    50                  55                  60
aag ccg gca aag gca gcc cgc tcc gtc cgt gcc cag cgc cac acc gac       240
Lys Pro Ala Lys Ala Ala Arg Ser Val Arg Ala Gln Arg His Thr Asp
 65                  70                  75                  80 atg ccc aag act cag aag gaa gta cat ttg aag aac aca agt aga ggg       288
Met Pro Lys Thr Gln Lys Glu Val His Leu Lys Asn Thr Ser Arg Gly
                     85                  90                  95 agt gca gga aac aag aac tac agg atg taggaagacc cttctgagga             335
Ser Ala Gly Asn Lys Asn Tyr Arg Met
                    100                 105 gtgaagaagg acaggccacc gcaggaccct ttgctctgca cagttacctg taaacattgg     395
aataccggcc aaaaaataag tttgatcaca tttcaaagat ggcatttccc ccaatgaaat     455
acacaagtaa acattc                                                    471

<210> SEQ ID NO 26
<211> LENGTH: 105
<212> TYPE: PRT
<213> ORGANISM: Oryctolagus cuniculus

<400> SEQUENCE: 26

Gly Pro Glu Thr Leu Cys Gly Ala Glu Leu Val Asp Ala Leu Gln Phe
 1               5                  10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
 50                  55                  60

Lys Pro Ala Lys Ala Ala Arg Ser Val Arg Ala Gln Arg His Thr Asp
 65                  70                  75                  80

Met Pro Lys Thr Gln Lys Glu Val His Leu Lys Asn Thr Ser Arg Gly
                 85                  90                  95

Ser Ala Gly Asn Lys Asn Tyr Arg Met
                100                 105
```

USE OF THE INSULIN-LIKE-GROWTH FACTOR 1 SPLICE VARIANT MGF FOR THE PREVENTION OF MYOCARDIAL DAMAGE

This application is a continuation of U.S. patent application Ser. No. 13/362,987, filed Jan. 31, 2012, now abandoned, which is a continuation of U.S. patent application Ser. No. 11/723,493, filed Mar. 20, 2007, now abandoned, which is a divisional of U.S. patent application Ser. No. 10/504,078, filed Oct. 20, 2004, now abandoned, which is a U.S. national phase under 35 U.S.C. § 371 of International Patent Application No. PCT/GB03/00537, filed Feb. 6, 2003, which designated the U.S. and claims benefit of GB Application No. 0202906.4, filed Feb. 7, 2002, the entire contents of each of which is hereby incorporated by reference in this application.

FIELD OF THE INVENTION

This invention relates to the use of polypeptides derived from the sequence of the IGF-I splice variant MGF and polynucleotides encoding such polypeptides in the prevention of myocardial damage following ischemia and/or mechanical overload.

BACKGROUND OF THE INVENTION

Ischemic Heart Disease

Ischemia occurs when an artery supplying oxygenated blood to a muscle or other organ becomes occluded. This diminishes the ability of the affected organ to function and may involve cell death in the area whose blood supply is reduced.

Ischemic heart disease is a major cause of death. Even in those patients who survive a heart attack, the prospects of an active lifestyle are severely reduced due to the loss of cardiac muscle. Cardiac muscle, like skeletal muscle and the central nervous system, is a post-mitotic tissue. As there is virtually no cell replacement throughout life, there has to be an effective ongoing local repair mechanism. Local physical and free radical damage occurs even in healthy tissues and has to be repaired; otherwise the cell undergoes cell death that results in a permanent functional deficit.

In the heart, ischemia can result from an obstruction of the coronary arteries. This leads to cardiomyocytes in certain areas becoming deprived of blood and thus oxygen. They then commence to die. This means increased mechanical strain on the surviving myocardiocytes in the area becoming damaged, which also leads to cell death. Thus, cell death occurs both as a result of oxygen deprivation and as a result of undue mechanical strain. The region of cell death, or necrosis, is known as an infarct.

The MGF Splice Variant of IGF-I

Mammalian IGF-I polypeptides have a number of isoforms, which arise as a result of alternative mRNA splicing. Broadly, there are two types of isoform, liver-type isoforms and non-liver-type ones. Liver-type isoforms may be expressed in the liver or elsewhere but, if expressed elsewhere, are equivalent to those expressed in the liver. They have a systemic action and are the main isoforms in mammals. Non-liver-type isoforms are less common and some are believed to have an autocrine/paracrine action. The MGF isoform of the invention is of the latter type. The terminology for the IGF-I splice variants is based on the liver isoforms (Chew et al, 1995) and has not fully evolved to take into account those produced by non-liver tissues. The latter are controlled to some extent by a different promoter (promoter 1) to the liver IGF-I isoforms, which respond to hormones and are under the control of promoter 2.

In human skeletal muscle, we have cloned the cDNA of three IGF-I splice variants. With reference to FIG. 1, exons 1 and 2 are alternative leader exons with distinct transcription start sites which are differentially spliced to common exon 3. Exons 3 and 4 code for the mature IGF-I peptide (B, C, A and D domains) as well as the first 16 amino acids of the E domain. Exons 5 and 6 each encode an alternative part of a distinct extension peptide, the E domain. This is followed by the termination codons of precursor IGF-I, 3' untranslated regions and poly(A) addition signal sites.

In skeletal muscle, the mRNA of one of the three muscle IGF-I splice variants was only detectable in exercised and/or in damaged (stretched and/or electrically stimulated) muscle, and its expression is related to the level of muscle activity. We have named it Mechano Growth Factor (MGF). MGF mRNA is not detected in dystrophic skeletal muscle even when it is subjected to stretch.

MGF (FIG. 1; Yang et al, 1996; McKoy et al, 1999) has exons 4, 5 and 6 whilst the muscle-expressed liver-type IGF-I has exons 4 and 6. The other two splice variants found in human muscle have similar sequences to the liver systemic type of IGF-I. Notably, human MGF has a 49 base pair insert (E domain) which changes its reading frame at the carboxy end.

We have already identified MGF for the treatment of disorders of skeletal muscle, notably muscular dystrophy (WO97/33997; U.S. Pat. No. 6,221,842; Yang et al, 1996; McKoy et al, 1999), for the treatment of neurological disorders (WO01/136483) and for nerve repair (WO01/85781).

SUMMARY OF THE INVENTION

The Role of L.IGF-I and MGF in Cardiac Muscle

The pharmacology of local regulation of gene expression, including the signaling pathways via which cells respond to mechanical stimuli, represents a new and important area of study. Mechanical factors (both extrinsic and intrinsic) are involved in the switch in gene expression and the regulation of transcriptional and translation processes within the cardiac myocytes. Alterations in mechanical stimuli can bring about increased cardiac muscle growth (cardiac hypertrophy), which is initially an adaptive response to augment cardiac output. However, under certain conditions a transition to pathological hypertrophy can take place in which there is increased myocardial mass but decreased cardiac performance. The cells of the ventricles revert back to expressing the embryonic isoforms of the contractile genes, which results in more rapid energy utilization. To further exacerbate the problem, other forms of myocardial injury that can occur often result in myocyte cell death (apoptosis) resulting in the loss of functioning myocytes. The remaining healthy myocytes generally increase in size in order to maintain cardiac output. This again leads to a hypertrophic state and can also develop to the point when it becomes a pathological condition.

There is evidence of the importance of systemic, liver-type IGF-I (L.IGF-I) as a regulator of myocardial growth and a protector against myocardial cell death. Significant improvement in cardiac function has been reported following growth hormone (GH) administration in animal models of cardiomyopathy and in clinical trials (Thuesen et al, 1998; Fazio et al, 1996). Growth hormone induces the expression of the systemic insulin-like growth factors via its action on the liver. Buerke et al (1995) reported that administration of recombinant L.IGF-I following transient myocardial ischemia in rats reduced cell death and cell membrane was reduced as indicated by CK washout. Using the general IGF-I antibody, Matthews et al (1999) showed that L.IGF-I was upregulated in the region of the infarct. The administration of growth hormone and recombinant liver type IGF-I in clinical trials have also been shown to have beneficial effects on cardiac output in terminal cardiac cases (Gluckman, WO92/11865). However, all of this work explicitly involved recombinant IGF-I of the liver or systemic type, or failed to recognise the existence of multiple IGF-I isoforms. None of it identified the MGF isoform.

Evidence concerning MGF in cardiac muscle, as opposed to L.IGF-I, heretofore been much less well developed. Using RT-PCR, Skarli et al (1998) found that MGF was expressed in rabbit cardiac muscle 24 hours after brief clamping of the aorta whilst only L.IGF was present in the resting heart and concluded that the MGF transcript was translated and produced by cardiac muscle in response to mechanical signals. Along with muscular dystrophy and other skeletal muscle disorders, WO97/3397 (U.S. Pat. No. 6,221,842) also mentions the possibility of prevention of cardiac disorders, diseases where promotion of cardiac muscle protein synthesis is a beneficial treatment, cardiomyopathies, acute heart failure or acute insult including myocarditis or myocardial infarction, and improving cardiac output by increasing heart/volume; but does not provide experimental findings linking MGF to cardiac, as opposed to skeletal, muscle.

Herein, we show that MGF is strongly expressed in the infracted area following ischemia in rat and sheep heart. In contrast to the situation for L.IGF-I, we have also shown that MGF expression coincides with the immediate recovery stage following mechanical overload and transient ischemia. MGF expression is therefore more rapid than L-IGF-I expression. We have also shown that MGF expression is induced in cardiac myocytes undergoing apoptosis, that stable transfection of the cardiac-like cell line H9C2 with MGF prevents apoptosis and obtained evidence that MGF induces a hypertrophic phenotype in myocytes in vitro.

Additionally, we have shown that prolonged expression of MGF in cardiac myocytes is associated with suppression of thick filament proteins of myofilaments but not thin filament proteins. This acts to dedifferentiate the myocyte. We conclude that MGF expression results in remodeling of the infracted region, i.e. that by dedifferentiating the myocyte, MGF facilitates the repair process.

We find that the E domain (part of exon 4) is important in cardiac muscle for local tissue repair, although this does not appear to involve stem cell activation as cardiac muscle is not believed to possess stem cells. Our data therefore suggest that the E domain insert in MGF not only changes the reading frame of the C-terminal end of the peptide from that of L.IGF-I but also that the E domain may have a separate function in cellular cardiomyocyte repair.

Our findings herein show that MGF is activated in response to cardiac tissue damage and has a repair function in the ischemic and/or overloaded heart. In turn, this shows that, in addition to previously noted utilities, can be used to protect against myocardial damage from apoptosis in response to ischemia/overload. In this connection, there are two aspects to the cardiac repair process, namely prevention of apoptosis and hypertrophy of the surviving cardiomyocytes in the damaged regions to compensate for the loss of cardiac muscle cells.

Rapid administration of an MGF polypeptide after a heart attack is particularly desirable, and longer term treatment can also be effected, especially by delivering an polynucleotide encoding an MGF polypeptide to maintain levels of MGF in the cardiac muscle after initial administration of the polypeptide.

Accordingly, the invention provides:
use of a Mechano Growth Factor (MGF) polypeptide or a polynucleotide encoding an MGF polypeptide in the manufacture of a medicament for the prevention or limitation of myocardial damage in response to ischemia or mechanical overload of the heart by preventing or limiting apoptosis in the myocardium;
a product comprising an MGF polypeptide and a polynucleotide encoding an MGF polypeptide for simultaneous, separate or sequential use in the prevention of myocardial damage in response to ischemia or mechanical overload of the heart; and
a method of preventing or limiting of myocardial damage in response to ischemia or mechanical overload of the heart, comprising administering to a subject that has suffered said ischemia or mechanical overload an effective amount of a Mechano Growth Factor (MGF) polypeptide or a polynucleotide encoding an MGF polypeptide.

This Figure shows the exon sequence of the IGF-I splice variants expressed in human skeletal muscle. Two of these have similar sequences to the systemic IGF-Is produced by the liver. Human MGF transcript has a 49 base (52 base in rat and rabbit) insert in the E domain which alters the reading frame and hence the C-terminal end of the peptide differs from that of the other splice variants.

Also shown is expression of the systemic IGF-I (A) and MGF (B) in the ischemic sheep heart. In the case of MGF the expression is more rapid and seen when the interval between the inducing the infarct and collecting the cardiac samples is relatively very short as in E3 in B.

Figure 2:
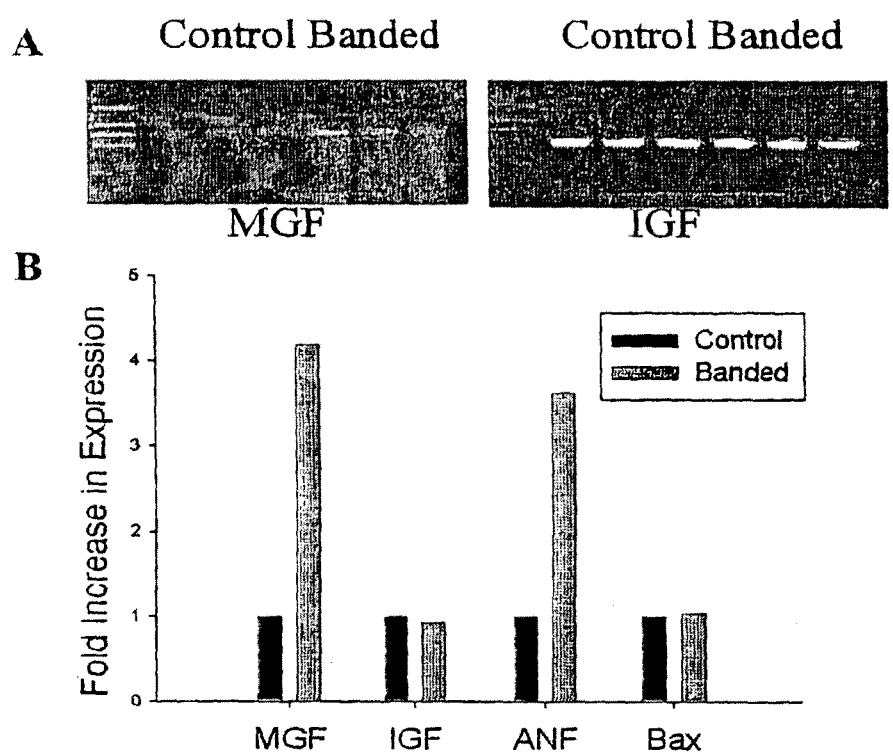

FIG. 2: Induction of MGF expression in aortic banded hearts

Groups of mice (3) were banded for 7 days following which MGF expression was assayed using quantitative real time RT-PCR in total RNA extracted form the heart. A. Results of the RT-PCR reaction run on agarose gels for MGF and IGF. B. Quantification of gene expression following real time RT-PCR, or MGF, IGF, ANF and Bax.

FIG. 3: Induction of the hypertrophic marker genes with overexpression of MGF

In the primary cardiac myocyte cultures transfected with the MGF (NT-GFP) plasmid there was a significant increase in the expression of both ANF and bMHC compared to the other conditions. This data shows that MGF expression is sufficient to induce a hypertrophic phenotype in vitro.

Figure 4:
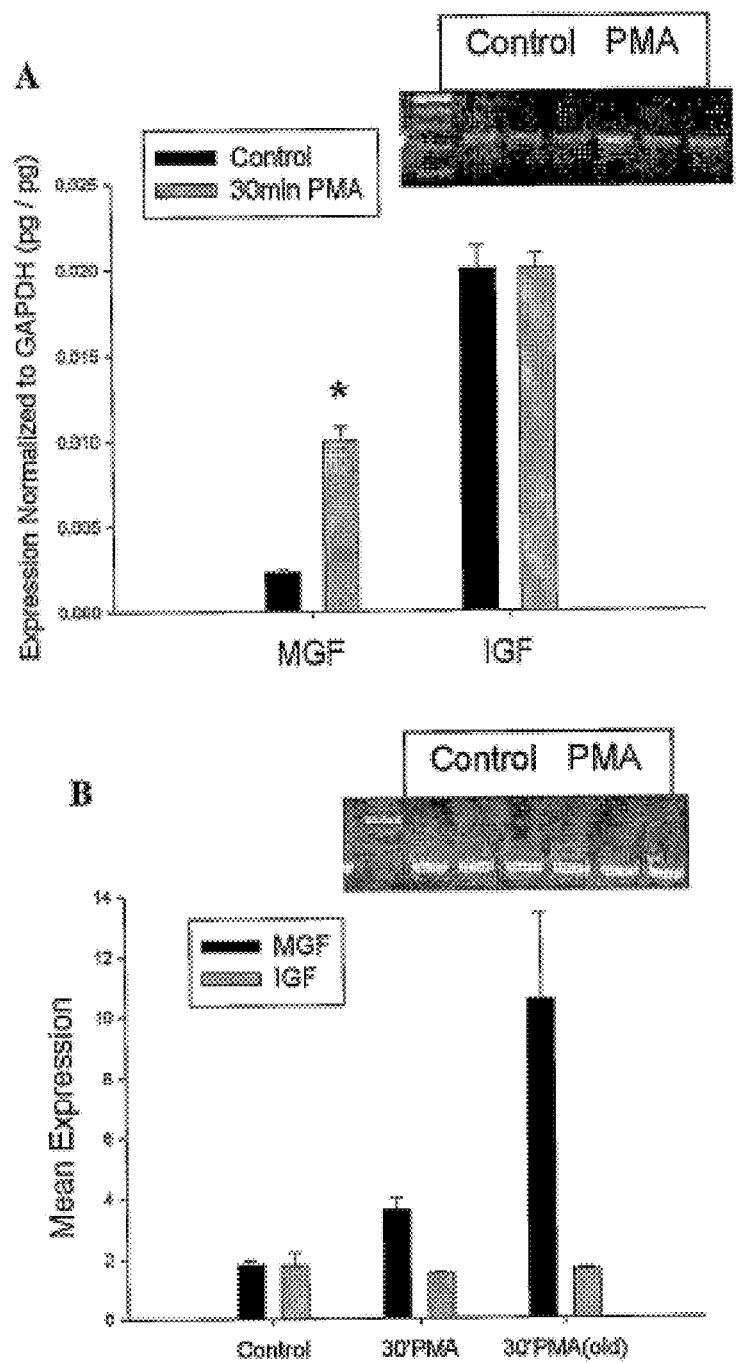

FIG. 4: Induction of MGF expression in response to MPA in cardiac myocytes

Primary cultures of cardiac myocytes were cultured in serum free media for 24 hours prior to the addition of PMA (200 nM). After 30 min total RNA was extracted and MGF gene expression was assayed using real time RT-PCR. A. MGF expression is significantly increased after PMA treatment, whereas IGF expression does not change. B. A repeat of the initial experiment but in the third group PMA was added to the cultures without changing the media. MGF expression is increased to a great extent than when PMA is added with fresh media.

Figure 5:
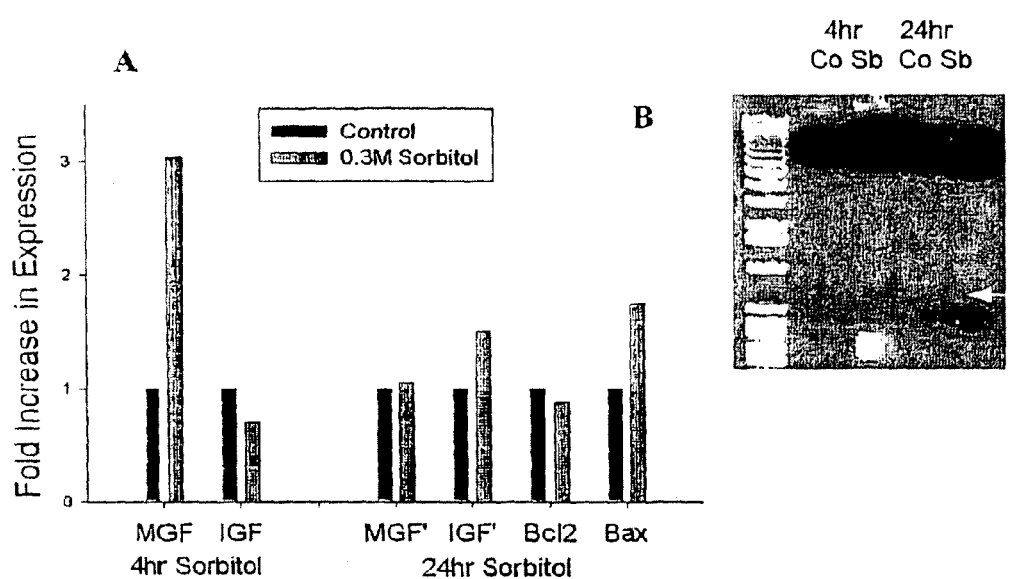

FIG. 5: MGF expression in cardiac myocytes under apoptotic conditions

Cardiac myocytes were cultured in serum free media for 24 hours prior to the addition of 0.3M sorbitol. Total RNA was extracted after 4 hours and 24 hours of treatments. A. Gene expression analysis was performed using real time RT-PCR for MGF, IGF, the anti-apoptosis marker Bcl2 and the apoptosis marker Bax. B. DNA was extracted from the same cells and subjected to electrophoresis to determine the extent of fragmentation. DNA fragmentation can be seen (arrow), in the 24 hour sorbitol treated cells indicating that apoptosis had taken place in those myocytes FIG. 6: Induction of apoptosis in cardiac cell line transfected with MGF and L.IGF Cells were stably transfected with cDNA encoding MGF and L.IGF-I and selected by resistance to antibiotic using standard techniques. Once clones were identified, these were isolated and expanded as separate lines of cells. Control cells, which had not been transfected, plus stable MGF and L.IGF-I clones were plated out and treated for 24 hours with 0.3M Sorbitol. Following treatment, DNA was extracted and subjected to electrophoresis (1% agarose) to determine if DNA fragmentation had occurred. Lanes 1 and 5 are DNA markers (100 bp and 1 kB respectively). Lane 2, control H9C2 cells after 24 hour sorbitol. Lane 3, MGF transfected H9C2 cells after 24 hour sorbitol. Lane 4, IGF transfected H9C2 cells after 24 hour sorbitol. It can be clearly seen that DNA fragmentation takes place in the control cells which are undergoing apoptosis, whereas cells overexpressing either the MGF or L.IGF-I genes do not undergo apoptosis.

FIG. 7: cDNA and amino acid sequence of human MGF, showing its exon structure.

FIG. 8: cDNA and amino acid sequence of rat MGF, showing its exons structure.

FIG. 9: cDNA and amino acid sequence of rabbit MGF, showing its exon structure.

FIG. 10: cDNA and amino acid sequence of human L.IGF-I, showing its exon structure.

FIG. 11: cDNA and amino acid sequence of rat L-IGF-I, showing its exon structure.

FIG. 12: cDNA and amino acid sequence of rabbit L-IGF-I, showing its exon structure.

FIG. 13: Sequence alignment, illustrating exon structure of human, rat and rabbit MGF and L-IGF-I, and highlighting similarities and differences.

FIG. 14: Cardiac myocytes infected with MGF and IGF viruses for 24 hrs

A. Localisation of MGF to nucleus. B. Presence of L-IGF in nucleus but also throughout cytoplasm.

Figure 15:
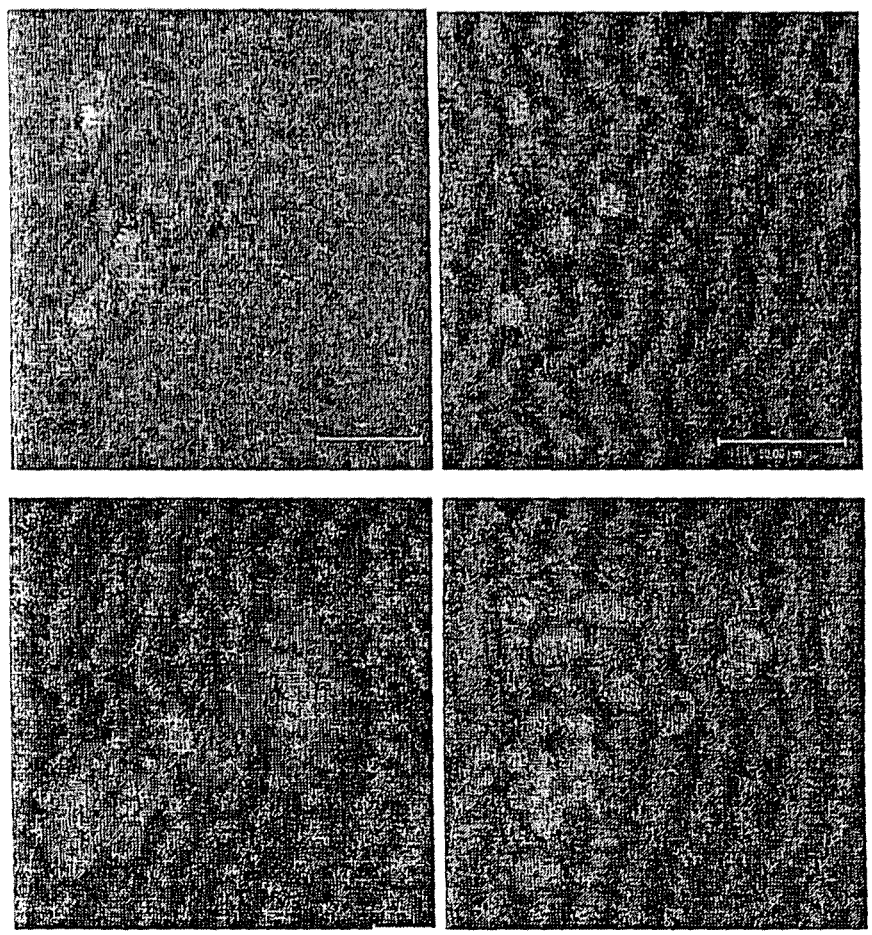

FIG. 15: Cardiac myocytes infected with MGF and IGF viruses and counter stained with DAPI Top-left. IGF-GFP virus. Top-right. Same with DAPI stain. Bottom-left. MGF-GFP virus. Bottom-right. Same with DAPI stain.

Figure 16:
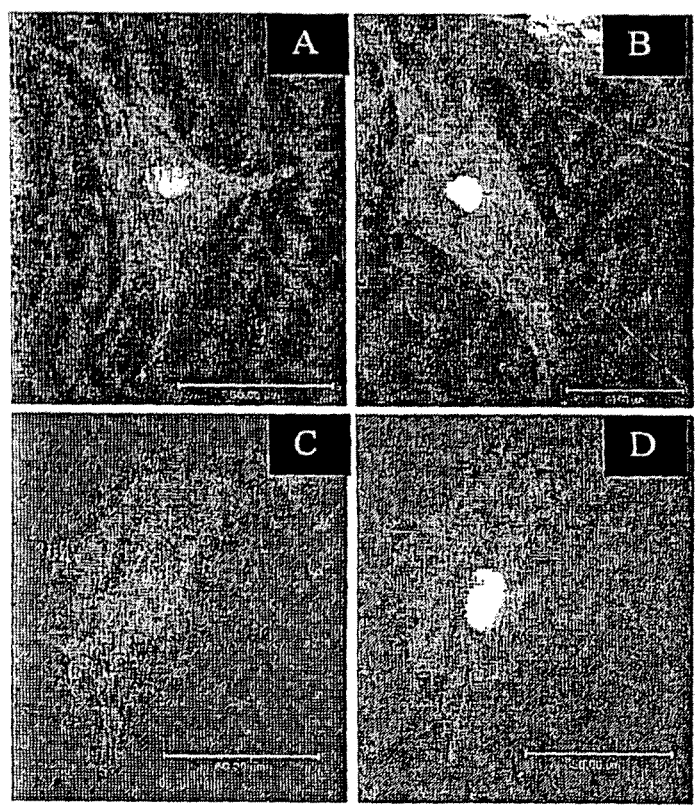

FIG. 16: Cardiac myocytes infected for 48 hrs with the MGF and control GFP expressing virus Cells were counter stained with phalloidin and DAPI to visualize the myofilaments. A. Control myocyte plus DAPI stain. B. GFP virus-infected myocyte. C. MGF virus-infected myocyte plus DAPI stain. D. MGF virus-infected myocyte.

Figure 17:
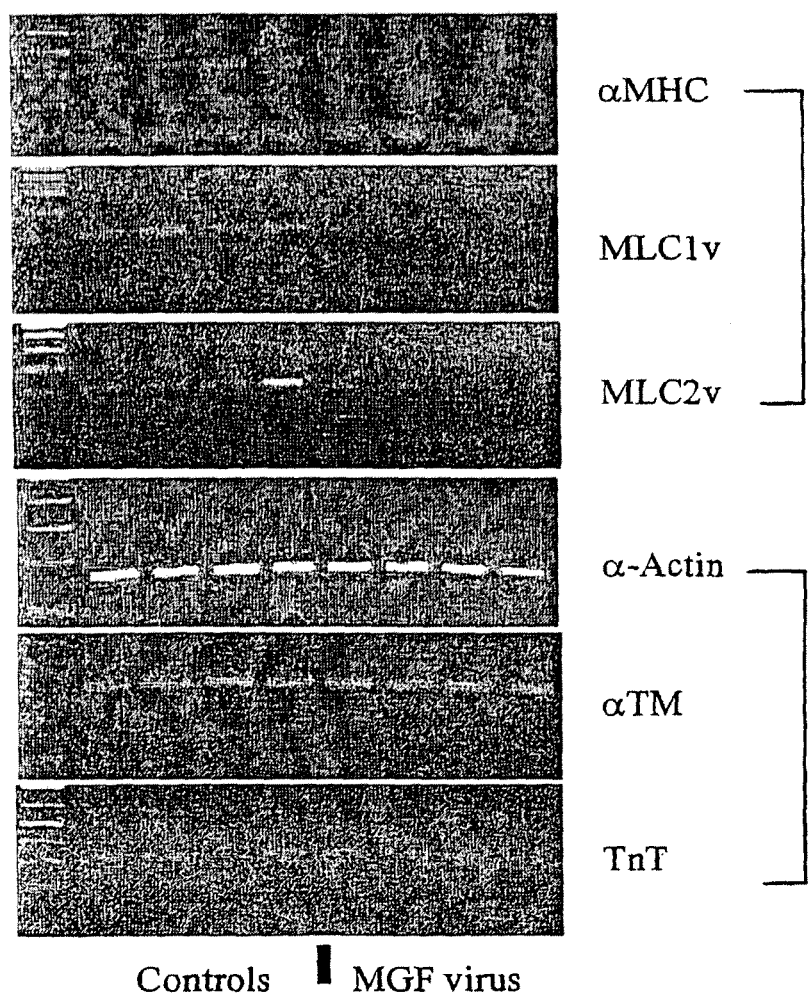

FIG. 17: Analysis of thick and thin filament expression with RT-PCR following 48 hrs of MGF viral infection in cardiac myocytes Upper three panels: thick filament proteins. Lower three panels: thin filament proteins.

Figure 18:
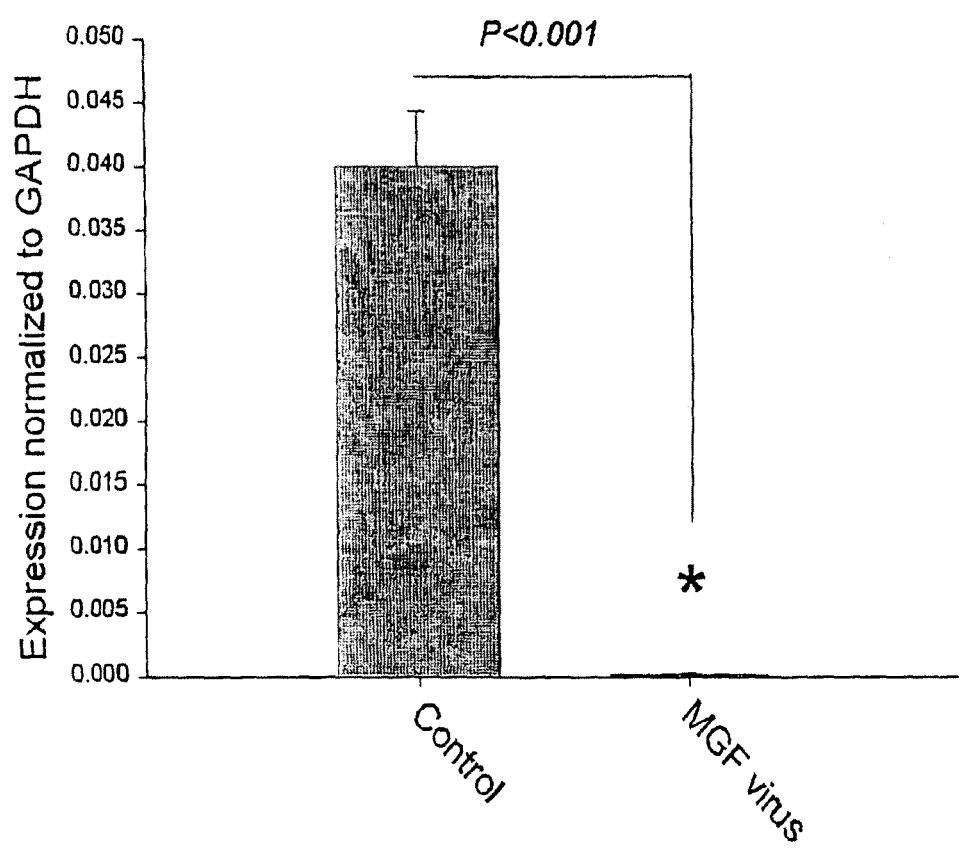

FIG. 18: Quantitative analysis of αMHC expression in cardiac myocytes following 48 hrs of MGF viral infection.

FIG. 19: Mean percentage of damaged-regenerating muscle fibre area in relation to the whole muscle section in two damage models A. Percentage of damaged/regenerated area relative to muscle mass. B. Percentage area stained with embryonic MyHC. Line with diamond points: bupivacaine; line with square points: stretch/stimulation.

FIG. 20: mRNA levels of MGF and IGF-IEa isoforms in two models of muscle damage A. MGF mRNA levels in picograms per microgram total RNA. B. IGF-IEa mRNA levels in picograms per microgram total RNA Line with diamond points: bupivacaine; line with square points: stretch/stimulation.

DETAILED DESCRIPTION OF THE INVENTION

MGF Polypeptides and Polynucleotides
Polypeptides
Background

MGF stands for mechano-growth factor (cf. McKoy et al, 1999). As discussed above, MGF is an alternatively spliced variant of IGF-I. Liver-type IGF-I (L.IGF-I) comprises amino acids encoded by exons 4 and 6 whereas MGF comprises amino acids encoded by exons 4, 5 and 6. MGF also has an altered reading frame at its carboxy terminus as a result of a 49 (human) or 52 (rat, rabbit) bp insert in exon 5, and is smaller because it is not glycosylated. Chew et al (1995) and Yang et al (1996) did not use the term MGF, but rather IGF-I Ec, to define the 4-5-6 splice variant. The muscle isoform that has the Ec domain is now known as MGF (cf McKoy et al, 1999; WO01/136483; WO01/85781).

Structual Properties of MGF Polypeptides of the Invention

Herein, an MGF polypeptide is understood to be any IGF-I polypeptide having the 4-5-6 exon structure or being derived from an IGF-I polypeptide with the 4-5-6 exon structure and one or more of the functional properties of MGF described herein or already identified by the Inventors, e.g. as in WO97/33997 and/or WO01/136483 and/or WO01/85781. The exon structure of MGF in human, rat and rabbit is illustrated in FIGS. 7, 8 and 9 (SEQ ID NOs. 1/2, 3/4 and 5/6). For comparison, the exon structure of human, rat and rabbit L.IGF-I is given in FIGS. 10, 11 and 12 (SEQ NOs. 9/10, 11/12 and 13/14), and a comparison between MGF and L.IGF-I is made in FIG. 13.

Preferably, MGF polypeptides of the invention will have the reading frame which, in native MGF, is generated by the 49/52 bp insert mentioned above. Preferably, MGF polypeptides of the invention will not be glycosylated. However, they may be glycosylated or partially glycosylated in some embodiments. By partially glycosylated is meant up to 10, 20, 30, 50, 70, 80, 90, 95 or 99% as much glycosylation as L.IGF-I, e.g. containing some, but not all, of L.IGF-I's glycosylation sites. The pattern of glycosylation may be the same as that of L.IGF-I in terms of the type and placement of sugars or it may be different.

Preferably, MGF polypeptides of the invention comprise sequences encoded by exons 3, 4, 5 and 6 or equivalent sequences. Optionally, they may include exons 1 and/or 2, or equivalent sequences as well. However, they may also be shorter, e.g. comprising only sequences encoded by exons 5 and 6 or by exons 4, 5 and 6.

MGF polypeptides of the invention may find their origins in any species that has 4-5-6 spliced IGF-I. Thus, an MGF polypeptide of the invention may have the sequence of human MGF or represent a truncated form of human MGF. Such human MGF polypeptides are is generally preferred.

MGF polypeptides having the sequence of an animal MGF may also be used, e.g. rat, rabbit, mouse, cow, sheep, goat, chicken, dog, cat MGF. Preferably, the species origin of the MGF polypeptide used will be matched to the species of the subject to be treated. In particular, it is preferred to use human MGF polypeptides to treat human patients.

The sequences of exons 3, 4, 5 and 6 of human MGF (IGF-I-Ec) (SEQ ID NO. 1/2, FIG. 7), rat MGF (SEQ ID NO, 3/4, FIG. 8) and rabbit MGF (IGF-I Eb) (SEQ ID NO. 5/6, FIG. 9) are given below, together with their corresponding cDNA sequences. SEQ ID NOs. 1, 3 and 5 are the cDNAs; SEQ ID NOs. 2, 4 and 6 are the polypeptides. For comparison, the sequences of exons 3, 4 and 6 human (SEQ ID NO. 9/10, FIG. 10), rat (SEQ ID No. 11/12, FIG. 11) and rabbit (SEQ ID NO. 13/14, FIG. 12) liver-type IGF-I (L.IGF-I) are also given (see FIG. 13 in particular for comparison). Polypeptides having the sequences of SEQ ID NOs. 2, 4 and 6 may be used in preferred embodiments of the invention.

Functional Properties of MGF Polypeptides of the Invention

Herein, MGF polypeptides may have the functional properties identified by the Inventors in WO97/33997. In particular, they may have the ability to induce growth of skeletal muscle tissue. Similarly, as discussed herein, they may have the ability to upregulate protein synthesis needed for skeletal muscle repair and/or to activate satellite (stem) cells in skeletal muscle. Alternatively or additionally, MGF polypeptides of the invention may have the neurological properties previously identified by the Inventors in WO01/136483. Thus, they may have the capacity to effect motoneurone rescue. In particular, they may be able to reduce motoneurone loss following nerve avulsion by up to 20, 30, 40, 50, 60, 70, 80, 90, 95, 99 or 100% in a treated subject compared to an equivalent situation in a non-treated subject. Reduction of motoneurone loss by 70% or more, or 80% more (i.e. to 30% or less or 20% or less) is preferred. The degree of rescue may be calculated using any suitable technique, e.g. a known technique such as Stereology. As a specific test, the techniques used in WO01/136483, which rely on measuring motoneurone rescue in response to facial nerve avulsion in rats, may be used.

More preferably, an MGF polypeptide of the invention will have the ability to prevent or limit myocardial damage following ischemia or mechanical overload by preventing cell death, or apoptosis, of the muscle cells of the myocardium. Preferably, an MGF polypeptide of the invention will have the ability to completely prevent apoptosis in the area of cardiac muscle to which it is applied. However, apoptosis may also be only partially prevented, i.e. limited. Damage is limited if any reduction of damage is achieved compared to that which would have taken place without a treatment of the invention, e.g. if damage is reduced by 1% or more, 5% or more, 10% or more, 20% or more, 30% or more, 50% or more, 70% or more, 80% or more, 90% or more, 95% or more, 98% or more, or 99% or more, as measured by the number or proportion of cells which die, or by the size of the area of muscle that loses function, or by the overall ability of the heart to pump blood.

In particular, reduction of damage can be estimated in vivo by determining cardiac output, ejection fraction etc using minimally invasive methods. Markers such as creatine kinase and troponin T in the serum can also be assayed. These are the parameters used in clinical situations to determine the extent damage to the cardiac muscle following injury.

The ability to prevent apoptosis may be measured by any suitable technique. For example, with reference to Example 4 and FIGS. 3 and 6, it may be measured by the ability to prevent apoptosis in a cardiac muscle cell or cardiac-like cell line, as indicated by DNA fragmentation. This may be assessed, in particular, in a cardiac-like cell line such as H9C2 stably transfected with a vector which expresses the MGF polypeptide. The ability to prevent aptosis, as indicated by DNA fragmentation, may be tested by treating the cells with sorbitol or another agent that places the cells under osmotic stress for up to, e.g. 1, 2, 4, 6, 12, 24 or 48 hours, preferably 12 to 24 hours, more preferably 24 hours, and investigating whether the pattern of fragmentation associated with apoptosis can be observed. An MGF polypeptide of the invention expressed in this way will typically reduce, preferably eliminate, DNA fragmentation under these conditions, as compared to an untransfected or sham-transfected (vector but no MGF coding sequence) after 6, 12 or 24 hours' sorbitol treatment.

The absence of expression, or low expression, of genes that act as markers for apoptosis can also act as an indication of prevention of apoptosis. One suitable marker is the Bax gene. Similarly, increased expression of anti-apoptosic markers in MGF-transfected cells under apoptotic conditions can be taken as a sign that the polypeptide of the invention is preventing apoptosis. One suitable anti-apoptotic marker gene is Bcl2.

The ability to prevent apoptosis may also be measured by reference to an MGF polypeptide's ability to prevent a reduction in cell number in myocyte cells in vitro. For example, cells can be transfected with a vector encoding the MGF polypeptide, such that it is overexpressed. Then, cell counts in MGF-transfected and control cultures can be compared over time under apoptotic conditions. Preferably, cells will die of less quickly in the MGF-transfected cultures, leaving greater proportion of the original number of cells in these cultures after, e.g. 24, 48 or 72 hours. For example up to 5% or more, 10% or more, 20% or more or 50% or more cells may remain in the MGF-transfected cultures after 24, 48 or 72 hours than in the control cultures.

Another preferred property of MGF polypeptides of the invention is the ability to induce a hypertrophic phenotype in cardiac muscle cells. In particular, this may be tested by assessing the ability to induce a hypertrophic phenotype in primary cardiac myocyte cultures in vitro. For example, such cultures can be transfected with a vector, e.g. a plasmid, encoding the MGF polypeptide such that the polypeptide of the invention is overexpressed, and the ability to induce hypertrophic phenotype determined. A preferred method for determining this is to test for an increase in expression of ANF (Atrial Natriuretic Factor) and/or bMHC (Beta Myosin Heavy Chain). ANF is an embryonic marker gene that is upregulated in hypertrophic conditions. bMHC is an important contractile protein in muscle.

MGF polypeptides having the sequence of naturally occurring MGFs are preferred. However, variant MGFs having the same basic 4-5-6 exon structure and properties may also be used.

Sequence of Polynucleotides of the Invention

Polypeptides of the invention may be encoded by polynucleotides as described below.

An MGF polypeptide of the invention may consist essentially of the amino acid sequence set out in SEQ ID NO. 2, 4 or 6 or a substantially homologous sequence, or of a fragment of either of these sequences, as long as the functional properties of the invention are maintained. In general, the naturally occurring amino acid sequences shown in SEQ ID NOs. 2, 4 and 6 are preferred. However, the polypeptides of the invention include homologues of the natural sequences, and fragments of the natural sequences and of their homologues, which have one or more of the functional properties of MGF, as defined herein.

In particular, a polypeptide of the invention may comprise:
- (a) the polypeptide sequence of SEQ ID NO. 2 (FIG. 7, human MGF), 4 (FIG. 8, rat MGF), or 6 (FIG. 9, rabbit MGF);
- (b) a polypeptide sequence at least 70, 80, 90, 95, 98 or 99% homologous to, a polypeptide of (a);
- (c) a sequence comprising the amino acids encoded wholly or partly by exons 5 and 6, 4, 5 and 6 or 3, 4, 5 and 6 of human, rat or rabbit MGF DNA of SEQ ID NO. 1, 3, or 5; or a sequence having 70% or greater homology thereto;
- (d) a sequence encoded by a nucleic acid sequence capable of selectively hybridising to a sequence of (a), (b) or (c); or
- (e) an allelic variant or species homologue of a sequence of (a).

Allelic Variants

An allelic variant will be a variant which occurs naturally and which will function in a substantially similar manner to the protein of SEQ ID NO. 2, 4 or 6 as defined above. Similarly, a species homologue of the protein will be the equivalent protein which occurs naturally in another species. Such a homologue may occur in any species, preferably a mammalian species, for example a bovine, equine, ovine, feline or canine species; such as cow, horse, sheep or goat, cat, or dog; or in a rodent species other than rat (SEQ ID NO. 4) or rabbit (SEQ ID NO. 6), or in a primate species other than human (SEQ ID NO. 2). Non-mammalian MGFs, for example piscine or avian MGFs, e.g. chicken MGF, are also MGFs of the invention. Within any one species, a homologue may exist as several allelic variants, and these will all be considered homologues of the protein of SEQ ID NO. 2, 4 or 6.

Allelic variants and species homologues can be obtained by methods known in the art, e.g. by probing suitable cell source with a probe derived from SEQ ID NO. 1, 3 or 5. Clones obtained can be manipulated by conventional techniques to generate a polypeptide of the invention which can be produced by recombinant or synthetic techniques known per se.

Homologues

A polypeptide of the invention is preferably at least 70% homologous to the protein of SEQ ID NO. 2, 4 or 6 more preferably at least 80 or 90% and more preferably still at least 95, 97 or 99% homologous thereto over a region of at least 20, preferably at least 30, for instance at least 40, 60 or 100 or more contiguous amino acids. Methods of measuring protein homology are well known in the art and it will be understood by those of skill in the art that in the present context, homology is calculated on the basis of amino acid identity (sometimes referred to as "hard homology").

Degrees of homology can be measured by well-known methods, as discussed herein for polynucleotide sequences.

The sequence of the polypeptides of SEQ ID NOs. 2, 4 and 6 and of the allelic variants and species homologues can be modified to provide further polypeptides of the invention.

Substitutions

Amino acid substitutions may be made, for example from 1, 2 or 3 to 10, 20 or 30 substitutions. For example, a total of up to 1, 2, 5, 10 or 20 amino acids may be substituted over a length of 50, 100 or 200 amino acids in the polypeptides. For example, up to 20 amino acids substituted over any length of 50 amino acids. The modified polypeptide generally retains one or more of the functional properties of MGF, as defined herein. Conservative substitutions may be made, for example according to the following table. Amino acids in the same block in the second column and preferably in the same line in the third column may be substituted for each other.

| ALIPHATIC | Non-polar | G A P |
| --- | --- | --- |
|  |  | I L V |
|  | Polar-uncharged | C S T M |
|  |  | N Q |
|  | Polar-charged | D E |
|  |  | K R |
| AROMATIC |  | H F W Y |

Fragments

Polypeptides of the invention also include fragments of the above-mentioned full length polypeptides and variants thereof, including fragments of the sequence set out in SEQ NOs. 2, 4 and 6.

Suitable fragments will generally be at least about 20, e.g. at least 20, 30, 40, 50, 60, 70, 80, 90 or 100 amino acids in size. Polypeptide fragments of the polypeptides of SEQ ID NOs. 2, 4 and 6 and allelic and species variants thereof may contain one or more (e.g. 2, 3, 5, 5 to 10 or more) substitutions, deletions or insertions, including conservative substitutions. Each substitution, insertion or deletion may be of any length, e.g. 1, 2, 3, 4, 5, 5 to 10 or 10 to 20 amino acids in length.

In particular, fragments of the invention may comprise the amino acids encoded by exons 5 and 6 or 4, 5 and 6 of human, rat or rabbit DNA of SEQ ID NO. 1, 3 or 5. The first amino aid of exon 4, Asn, is partly encoded by exon 3 (1 nucleotide) and partly by exon 4 (2 nucleotides). It is preferred that said first amino acid be present, in a fragment of the invention.

Chimeric Sequences

MGF polypeptides encoded by chimeric polynucleotide sequences of the invention (see below) may be used.

Isolation, Purification and Modification

Polypeptides of the invention may be in a substantially isolated form. It will be understood that the polypeptide may be mixed with carriers or diluents which will not interfere with the intended purpose of the polypeptide and still be regarded as substantially isolated. A polypeptide of the invention may also be in a substantially purified form, in which case it will generally comprise the polypeptide in a preparation in which more than 70%, e.g. more than 80, 90, 95, 98 or 99% of the polypeptide in the preparation is a polypeptide of the invention.

Polypeptides of the invention may be provided in a form such that they are outside their natural cellular environment. Thus, they may be substantially isolated or purified, as discussed above, or in a cell which they do not occur in nature, e.g. a cell or other plant species, animals, yeast or bacteria.

Polypeptides of the invention may be modified for example by the addition of Histidine residues or a T7 tag to assist their identification or purification or by the addition of a signal sequence to promote their secretion from a cell.

A polypeptide of the invention may be labelled with a revealing label. The revealing label may be any suitable label which allows the polypeptide to be detected. Suitable labels include radioisotopes, e.g. $^{125}$I, $^{35}$S, enzymes, antibodies, polynucleotides and linkers such as biotin.

Polypeptides of the invention may be chemically modified, e.g. post-translationally modified. For example, they may comprise modified amino acid residues. They may also be glycosylated (see above), though MGF is not naturally glycosylated. Such modified polypeptides will be understood to be polypeptides of the invention.

The effects of modifications to MGF's sequence can be tested by any suitable method. For example, the binding properties and/or stability of variant MGFs can be tested by comparing them in vitro or in vivo to those of unmodified MGF.

Polynucleotides

Polynucleotides of the invention encode polypeptides of the invention.

Preferred polynucleotides of the invention comprise a coding sequence encoding a polypeptide having one or more of the functional properties of MGF, as defined herein, which coding sequence is selected from:

(a) the coding sequence of any one of SEQ ID NO. 1, 3 or 5;
(b) the coding sequence of exons 5 and 6, 4, 5 and 6 or exons 3, 4, 5 and 6 of any one of SEQ ID NO. 1, 3 or 5
(c) a sequence capable of selectively hybridising to a sequence of (a) or (b), or to a sequence complementary to a sequence of (a) or (b);
(d) a sequence having 70% or more homology to a sequence of (a) or (b);
(e) a sequence which is a fragment of the sequence of any one of (a) to (d); and
(f) a sequence which differs from that of any one of (a) to (d) but which, owing to the degeneracy of the genetic code, encodes the same polypeptide.

Thus, the invention provides polynucleotides comprising the coding sequence as shown in any one of SEQ ID NO. 1, 3 or 5 and variants thereof with related sequences. Polynucleotides of the invention can be used to prepare vectors of the invention.

SEQ ID NOs. 1, 3 and 5

Preferred polynucleotides of the invention comprise coding sequences as shown in SEQ ID NOs. 1, 3 and 5.

Hybridisable Sequences

A polynucleotide of the invention may hybridise selectively to coding sequence of SEQ ID NO. 1, 3 or 5 at a level significantly above background. Background hybridisation may occur, for example because of other cDNAs present in a cDNA library. The signal level generated by the interaction between a polynucleotide of the invention and the coding sequence of SEQ ID NO, 1, 3, 5, 7, 9 or 11 is typically at least 10 fold, preferably at least 100 fold, as intense as interactions between other polynucleotides and the corking sequence of SEQ ID NO, 1, 3 or 5. The intensity of interaction may be measured, for example by radiolabelling the probe, e.g. with $^{32}$P. Selective hybridisation is typically achieved using conditions of medium to high stringency (for example 0.03M sodium chloride and 0.03M sodium citrate at from about 50° C. to about 60° C., for example 45 to 50, 50 to 55 or 55 to 60° C., e.g. at 50 or 60° C.

However, such hybridisation may be carried out under any suitable conditions known in the art (see Sambrook et al, 1989, *Molecular Cloning: A Laboratory Manual*). For example, if high stringency is required, suitable conditions include 0.2×SSC at around 60° C., for example 40 to 50° C., 50 to 60° C. or 60 to 70° C., e.g. at 50 or 60° C. If lower stringency is required, suitable conditions include 2×SSC at around 60° C., for example 40 to 50° C., 50 to 60° C. or 60 to 70° C., e.g. at 50 or 60° C.

Stringency typically occurs in a range from about Tm-5° C. (5° C. below the melting temperature (Tm) of the two sequences hybridising to each other in a duplex) to about 20° C. to 25° C. below Tm. Thus, according to the invention, a hybridisable sequence may be one which hybridises to SEQ ID NO. 1, 3 or 5 at a temperature of from Tm to Tm-25° C., e.g. Tm to Tm-5° C., Tm-5 to Tm-10° C., Tm-10 to Tm-20° C. or Tm-20 to Tm-25° C.

Homologous Sequences

A polynucleotide sequence of the invention, will comprise a coding sequence at least 70% preferably at least 80 or 90% and more preferably at least 95, 98 or 99%, homologous to the coding sequence of SEQ ID NO. 1, 3 or 5.

Such homology will preferably apply over a region of at least 20, preferably at least 50, for instance 100 to 500 or more, contiguous nucleotides.

Methods of measuring nucleic acid and polypeptide homology are well known in the art. These methods can be applied to measurement of homology for both polypeptides and nucleic acids of the invention. For example, the UWGCG Package provides the BESTFIT program which can be used to calculate homology (Devereux et al, 1984, *Nucleic Acids Research* 12, p. 387-395).

Similarly, the PILEUP and BLAST algorithms can be used to line up sequences (for example as described in Altschul, S. F., 1993, *J. Mol. Evol.* 30:290-300; Altschul, S. F. et al, 1990) *J. Mol. Biol.* 215:403-410).

Many different settings are possible for such programs. According to the invention, the default settings may be used.

In more detail, the BLAST algorithm is suitable for determining sequence similarity and it is described in Altschul et al (1990) *J. Mol. Biol.* 215:403-410. Software for performing BLAST analyses is publicly available through the National Center for Biotechnology Information (http://www.ncbi/nlm.hih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci. USA* 89:10915-10919) alignments (B) of 50, expectation (E) of 10, M=5, N=4, and a comparison of both strands.

The BLAST algorithm performs a statistical analysis of the similarity between two sequences; see e.g. Karlin and Altschul (1993) *Proc. Natl. Sci. USA* 90:5873-5787. One measure of similarity provided by the BLAST algorithm is the smallest sum probability (P(N)), which provides an indication of the probability by which a match between two nucleotide or amino acid sequences would occur by chance. For example, a nucleic acid is considered similar to a fused gene or cDNA if the smallest sum probability in comparison of the test nucleic acid to a fused nucleic acid is less than about 1, preferably less than about 0.1, more preferably less than about 0.01, and most preferably less than about 0.001.

Fragments

Also included within the scope of the invention are sequences which are fragments of the sequences of (a) to (d) above but which encode MGF polypeptides having the properties discussed herein.

In particular, fragments may comprise exons 5 and 6 or 4, 5 and 6 or exons 3, 4, 5 and 6 of human, rat or rabbit MGF DNA of SEQ ID NO. 1, 3 or 5.

The first amino acid of exon 4, Asn, is partly encoded by exon 3 and partly by exon 4. It is preferred that the necessary coding bases from exon 3 are present to encode said first amino acid, Asn.

Degenerate Sequences

Also included within the scope of the invention are sequences that differ from those of (a) to (e) but which, because of the degeneracy of the genetic code, encode the same protective polypeptides. For example, the invention provides degenerate variants of the sequence of SEQ ID NOs. 1, 3 and 5 that also encode the polypeptide of SEQ ID NOs. 2, 4 and 6.

Complementary Sequences

In addition, the invention provides polynucleotides having sequences complementary to any of the above-mentioned sequences.

Chimeric Sequences

Chimeric sequences comprising exons from more than one species may also be used. For example, one or more of exons 3 to 6 may be derived from human and one or more from rat and/or rabbit.

Further Properties

The nucleic sequences of the invention may be of any length as long as they encode a polypeptide of the invention. A nucleic acid sequence according to the invention may be a contiguous fragment of the sequence of SEQ ID NO. 1, 3 or 5 or a sequence that is related to it in any of the ways described above. Alternatively, nucleic acids of the invention may comprise DNA sequences that are not contiguous in the sequence of SEQ ID NO. 1, 3 or 5. These sequences may be fragments of the sequence of SEQ ID NO. 1, 3 or 5 or nucleic acid sequences that are related to such fragments in any of the ways described above. Nucleic acid sequences of the invention will preferably comprise at least 50 bases or base pairs, for example 50 to 100, 100 to 500, 500 to 1000 or 1000 to 2000 bases or base pairs.

Any combination of the above-mentioned degrees of homology and minimum sizes may be used to defined polynucleotides of the invention, with the more stringent combinations (e.g. higher homology over longer lengths and/or hybridisation under more stringent conditions) being preferred. Thus, for example a polynucleotide which is at least 90% homologous over 100 nucleotides forms one aspect of the invention, as does a polynucleotide which is at least 95% homologous over 100 or 200 nucleotides.

Polynucleotides of the invention may comprise DNA or RNA. They may also be polynucleotides which include within them synthetic or modified nucleotides. A number of different types of modification to polynucleotides are known in the art. Modifications may, for example enhance resistance to nucleases and/or enhance ability to enter cells. For example, phosphorothioate oligonucleotides may be used. Other deoxynucleotide analogs include methylphosphonates, phosphoramidates, phosphorodithioates, N3'P5'-phosphoramidates and oligoribonucleotide phosphorothioates and their 2'-O-alkyl analogs and 2'-O-methylribonucleotide methylphosphonates. A further possible modification is the addition of acridine or polylysine chains at the 3' and/or 5' ends of the molecule.

Alternatively mixed backbone oligonucleotides (MBOs) may be used. MBOs contain segments of phosphothioate oligodeoxynucleotides and appropriately placed segments of modified oligodeoxy- or oligoribonucleotides. MBOs have segments of phosphorothioate linkages and other segments of other modified oligonucleotides, such as methylphosphonate, which is non-ionic, and very resistant to nucleases or 2'-O-alkyloliogoribonucleotides. For the purposes of the present invention, it is to be understood that the polynucleotides described herein may be modified by any method available in the art. Such modifications may be carried out in order to enhance the in vivo activity or lifespan of polynucleotides of the invention.

Polynucleotides of the invention may be used to produce a primer, e.g. a PCR primer, a primer for an alternative amplification reaction, a probe, e.g. labelled with a revealing label by conventional means using radioactive or non-radioactive labels, or the polynucleotides may be cloned into vectors. Such primers, probes and other fragments will preferably be at least 10, preferably at least 15 or 20, for example at least 25, 30 or 40 nucleotides in length. These will be useful in identifying species homologues and allelic variants as discussed above.

Polynucleotides such as a DNA polynucleotides and primers according to the invention may be produced recombinantly, synthetically, or by any means available to those of skill in the art. They may also be cloned by standard techniques. The polynucleotides are typically provided in isolated and/or purified form.

In general, primers will be produced by synthetic means, involving a stepwise manufacture of the desired nucleic acid sequence one nucleotide at a time. Techniques for accomplishing this using automated techniques are readily available in the art.

Genomic clones corresponding to the cDNAs of SEQ ID NOs. 1, 3 and 5 containing, for example introns and promoter regions are also aspects of the invention and may also be produced using recombinant means, for example using PCR (polymerase chain reaction) cloning techniques.

The 4-5-6 exon pattern of MGF is characteristic of polynucleotides of the invention. Any suitable method may be used to ensure that this pattern is reflected in the coding sequence, and thus in the encoded polypeptide. For example, cDNA sequences lacking introns and splice signals and including the coding sequences of exons 4, 5 and 6 may be used. Alternatively, genomic DNA may be used if it will be correctly spliced in the situation at hand.

Although in general the techniques mentioned herein are well known in the art, reference may be made in particular to Sambrook et al (1989), *Molecular Cloning: A Laboratory Manual*.

Polynucleotides which are not 100% homologous to the sequences of the present invention but fall within the scope of the invention, as described above, can be obtained in a number of ways, for example by probing cDNA or genomic libraries from other plant species with probes derived from SEQ ID NO. 1, 3 or 5. Degenerate probes can be prepared by means known in the art to take into account the possibility of degenerate variation between the DNA sequences of SEQ ID NO. 1, 3 or 5 and the sequences being probed for under conditions of medium to high stringency (for example 0.03M sodium chloride and 003M sodium citrate at from about 50° C. to about 60° C.), or other suitable conditions (e.g. as described above).

Allelic variants and species homologues may also be obtained using degenerate PCR which will use primers designed to target sequences within the variants and homologues encoding likely conserved amino acid sequences. Likely conserved sequences can be predicted from aligning the amino acid sequences of the invention (SEQ ID NO. 2, 4 or 6) with each other and/or with those of any homologous sequences known in the art. The primers will contain one or more degenerate positions and will be used at stringency conditions lower than those used for cloning sequences with single sequence primers against known sequences.

Alternatively, such polynucleotides may be obtained by site-directed mutagenesis of sequences of SEQ ID NO. 1, 3 or 5 or allelic variants thereof. This may be useful where, for example silent codon changes are required to sequences to optimise codon preferences for a particular host cell in which the polynucleotide sequences are being expressed. Other sequences may be desired in order to introduce restriction enzyme recognition sites, or to alter the properties or function of the polypeptides encoded by the polynucleotides.

The invention further provides double stranded polynucleotides comprising a polynucleotide of the invention and its complement.

Polynucleotides, probes or primers of the invention may carry a revealing label. Suitable labels include radiosotopes such as $^{32}P$ or $^{35}S$, enzyme labels, or other protein labels such as biotin. Such labels may be added to polynucleotides, probes or primers of the invention and may be detected using techniques known per se.

Treatments of the Invention
Ischemia and Mechanical Overload

It is an object of the invention to prevent or limit myocardial damage in response to ischemia or mechanical overload of the heart by preventing or limiting apoptosis in the myocardium using an MGF polypeptide or polynucleotide of the invention, or both. Ischemia occurs when an artery supplying oxygenated blood to a muscle or other organ becomes occluded. This diminishes the ability of the affected organ to function and may involve cell death in the area whose blood supply is reduced. In the heart, ischemia can result from an obstruction of the coronary arteries. This leads to cardiomyocytes in certain areas becoming deprived of blood and thus oxygen. They then commence to die. This means increased mechanical strain on the surviving myocardiocytes in the area becoming physically damaged, unless they undergo hypertrophy and adaptation. Thus, cell death occurs both as a result of oxygen deprivation and as a result of undue mechanical strain. The region of cell death, or necrosis, is known as an infarct. Overload means stretch of the injured part of the myocardium by the venous return as well as the increased contractile force required from a decreased number of cardiomyocytes. If cardiac muscle cells are overstretched this results in the actin and myosin filaments being pulled out to the point at which they no longer overlap and the sarcomeres (the force generating units) are disrupted.

Delivery of MGF Polypeptides to Subjects for Prevention of Myocardial Damage

MGF polypeptides can be delivered to subjects in need of treatment by any suitable method. Generally, MGF polypeptides will be delivered intravenously as this is a safe and reliable method of delivery. Under appropriate clinical circumstances (e.g. in specialist cardiac units) direct delivery to the heart may also be possible, e.g. using a so-called "needle-less" injection system (e.g. provided by Powderject) to deliver the polypeptide to the heart.

Desirably, the MGF polypeptide will be administered as rapidly as possible after the onset of the ischemia or mechanical overload to the heart, for example as soon as a heart attack resulting from ischemia has been diagnosed. Preferably, it will be administered within 5, 10, 15, 30 or 60 minutes, or within 2 or 5 hours. Long term treatment can also be effected by re-administration of the polypeptide, but delivery of an MGF-encoding polynucleotide is preferred for that purpose (see below).

Preferably, the ischemia or mechanical overload in response to which the MGF polypeptide or polynucleotide is administered is a temporary condition.

In a particularly preferred embodiment, the MGF polypeptide is administered in response to a heart attack. Treatments of the invention will be particularly effective in helping heart attack sufferers make a good recovery; and to return to a normal, active lifestyle.

Production of MGF Polypeptides

MGF polypeptides may be produced in any suitable manner. In some embodiments they may be extracted from animal tissues. However, it is preferred that they be produced recombinantly. This can be done using known techniques.

Use of MGF Polynucleotides in Addition to MGF Polypeptides

In situations where both short-term and long-term delivery is desired, a polynucleotide encoding an MGF polypeptide of the invention may be delivered a well as the MGF polypeptide. MGF polypeptide-encoding may be delivered simultaneously with the polypeptide or separately. It may be delivered in the same pharmaceutical formulation or a different one and by the same route of administration or a different one. MGF has a short half-life and in vivo expression of MGF facilitates localisation and avoids the need for repeated injection to effect long-term therapy. Intramuscular administration, is preferred for polynucleotides of the invention, especially plasmids and other naked nucleic acids.

Vectors for Delivery of Polynucleotides

The polynucleotides of the invention may be delivered in any suitable manner. In particular, they will generally be delivered via a vector. Any suitable vector may be used.

The polynucleotide may be delivered in a "naked" form (e.g. in a plasmid vector), optionally associated with an agent to assist in its penetration, as discussed below. Alternatively, the vector may be one that encapsulates the nucleic acid, e.g. a virus. The vector may, for example, be a plasmid or cosmid vector, or another type of vector.

The vector may be a viral vector, such as a vector comprising a virus able to infect the cells of the recipient subject. Thus, the vector may be, or may be derived from any suitable virus, for example an alphavirus, adenovirus, adeno-associated virus, baculovirus, vaccinia virus, herpes virus, herpes simplex virus, retrovirus (e.g. lentivirus) vector, or baculovirus. A virus vector will be disabled, in the sense that it will not typically be able to replicate or cause pathological effects in the same way as on intact virus. It will typically be attenuated, for example replication defective.

Especially when it is delivered in a "naked" form, e.g. as a plasmid, the polynucleotide may be associated with an agent to assist in penetration of cells. Examples include cationic agents (e.g. cationic lipids), polylysine, lipids, and precipitating agents (e.g. a calcium salt). Such agents generally aid the passage of the polynucleotide across the cell membrane. The polynucleotide may be in the form of liposomes or particles, for example in association with any of the penetrating agents mentioned above. The polynucleotide may be in association with an agent that causes the polynucleotide to adopt a more compact form, such as a histone. The polynucleotide may be in association with spermidine.

Similarly, liposomes may be used to help transport polynucleotides of the invention into cells.

The polynucleotide may be associated with a carrier which can be used to deliver the polynucleotide into the cell, or even into the nucleus, using biolistic techniques. Such a carrier may be a metal particle, such as a gold or tungsten particle.

The polynucleotide is typically capable of being expressed in a cell of the recipient. Thus, the polynucleotide typically also comprises control sequences which are operably linked to the MGF coding sequence of the invention, said control sequences being capable of expressing the coding sequence in the cells of the recipient, for example after integration of the polynucleotide into the genome of the cell.

The control sequences typically comprise a promoter (generally 5' to the coding sequence) and/or a terminator and/or translation initiation sequence (e.g. GCCACCATGG (SEQ ID NO. 7) or GCCCCCATGG (SEQ ID NO. 8)) and/or a translational stop codon (e.g. TAA, TAG or TGA) and/or a polyadenylation signal and/or one or more enhancer sequences and/or a RNA pause site. The control sequences may enhance the transcription or translation of the polynucleotide. The control sequences may be tissue-specific so that the polynucleotide is only expressed in certain tissues, or may be the control sequences of a constitutively expressed gene. Muscle-specific promoters and enhancers are particularly preferred. The control sequences are typically those of any of the eukaryotes mentioned herein or of a virus which infects a eukaryote, e.g. of the species of the recipient, such as a human virus for a human recipient. The polynucleotide may comprise an origin of replication.

The promoter may, for example be (in particular for expression in mammalian cells) a metallothionein gene promoter, SV40 large T antigen promoter, CMV or adenoviral promoter.

So far as tissue-specific expression is concerned, muscle-specific control elements, such as muscle-specific promoters and enhancers, are particularly preferred, especially where the nucleic acid is to be delivered intramuscularly, e.g. in plasmid form. Such elements can be derived from, for example myosin genes. For example, myosin light chain or heavy chain promoters may be used, as may myosin light chain or heavy chain enhancers.

Several myosin enhancers and promoters have been identified to date from both myosin light chain and myosin heavy chain genes. Preferably, the myosin enhancer and/or promoter used is of vertebrate origin, more preferably avian, piscine or mammalian origin.

A myosin light chain enhancer is preferred. A rat myosin light chain 1/3 enhancer (Donoghue et al (1988) *Genes Dev.* 2:1779-1790; Neville et al (1996) *Dev. Genetics* 19:157-162) is especially preferred. The enhancer is operably linked to the promoter. The enhancer may be either upstream or downstream of the promoter. The enhancer may be used in either orientation.

A myosin heavy chain promoter is preferred. A particularly preferred myosin heavy chain promoter is a truncated rabbit β-cardiac myosin heavy chain promoter, in particular up to and including 789 base pairs upstream of the transcriptional start site. Another known myosin heavy chain promoter is the carp FG2 promoter, in particular up to and including 901 base pairs upstream of the transcription start site (Gauvry et al (1996) *Eur. J. Biochem.* 236:887-894). Further details of myosin heavy chain promoters derived from rat, rabbit, human, porcine and chick myosin heavy chain genes are given in Gauvry et al (1996) and references therein. All of these promoters may be used in the present invention.

However, any suitable regulatory elements may be used, and the ones mentioned above are merely exemplary.

In this context, and if appropriate to the overall condition of the patient, introduction of MGF of the invention may be linked with physical activity. As muscles respond to exercise and myosin is the most abundant protein in muscle the myosin promoter/enhancer regulatory elements means that the expression of the cDNA will be upregulated by increased muscular activity.

Plasmid vectors and disabled viral vectors are preferred embodiments. Plasmid vectors are particularly preferred, especially for intramuscular administration aimed at securing local expression in the muscle.

The vector may be designed for stable integration into the genome of the recipient's cells. Alternatively, it may be designed to be non-integrative. In stable introduction the polynucleotide becomes integrated into the genome of the cell (i.e. becomes contiguous with genome). Thus, the polynucleotide may also comprise a sequence which enhances integration of the polynucleotide such as the loxP sites of the bacteriophage P1 Cre recombination system, FRT sites of the yeast FLP recombination system or Adeno-associated virus (AAV) terminal repeat sequences.

Integration may be enhanced by other factors which are present, such as bacteriophage P1 derived Cre, yeast derived FLP recombinase, AAV Rep proteins, Cre or FLP recombinases or bacterial Rec proteins. In one embodiment, the polynucleotide of the invention is capable of expressing such a factor.

The polynucleotide may be one which integrates randomly (such as in a non-sequence specific manner) into any position in the genome or one which preferentially integrates at particular sites of the genome. Generally the whole coding sequence of the polynucleotide and the control sequences will be present in the genome after integration.

Pharmaceutical Compositions and Formulations

The polypeptides and polynucleotides of the invention are preferably delivered in the form of a pharmaceutical formulation comprising a pharmaceutically acceptable carrier or diluent. Any suitable pharmaceutical formulation may be used.

For example, suitable formulations may include aqueous and non-aqueous sterile injection solutions which may contain anti-oxidants, buffers, bacteriostats, bactericidal antibiotics and solutes which render the formulation isotonic with the bodily fluids of the intended recipient; and aqueous and non-aqueous sterile suspensions which may include suspending agents and thickening agents. The formulations may be presented in unit-dose or multi-dose containers. For example, sealed ampoules and vials, and may be stored in a frozen or freeze-dried (lyophilized) condition requiring only the addition of the sterile liquid carrier, for example water for injections, immediately prior to use.

It should be understood that in addition to the ingredients particularly mentioned above the formulations of this invention may include other agents conventional in the art having regard to the type of formulation in question. Sterile, pyrogen-free aqueous and non-aqueous solutions are preferred.

Dosages

The proteins, polynucleotides and vectors of the invention may be delivered in any suitable dosage, and using any suitable dosage regime. Persons of skill in the art will appreciate that the dosage amount and regime may be adapted to ensure optimal treatment of the particular condition to be treated, depending on numerous factors. Some such factors may be the age, sex and clinical condition of the subject to be treated.

The dosage used for the delivery of nucleic acids by vectors will depend on many factors, including the efficiency with which the vectors deliver the nucleic acids to cells, and the efficiency with which the nucleic acids are expressed in the cells.

For the delivery of naked nucleic acids (e.g. plasmids or other naked non-viral vectors), typical doses are from 0.1 to 5000 µg, for example 10 to 1000 µg, such as 10 to 100 µg, 100 to 500 µg and 500 to 2000 µg per dose.

As a guide, viral vectors may be delivered in doses of from $10^4$ to $10^{14}$ cfu or pfu/ml, for example $10^4$ to $10^6$, $10^6$ to $10^8$, $10^8$ to $10^{10}$, $10^{10}$ to $10^{12}$ or $10^{12}$ to $10^{14}$ cfu or pfu/ml. Doses in the region of $10^5$ to $10^9$ cfu or pfu/ml are preferred. The term pfu (plaque forming unit) applies to certain viruses, including adenoviruses, and corresponds to the infectivity of a virus solution, and is determined by infection of an appropriate cell culture, and measurement, generally after 48 hours, of the number of plaques of infected cells. The term cfu (colony forming unit) applies to other viruses, including retroviruses, and is determined by means known in the art generally following 14 days incubation with a selectable marker. The techniques for determining the cfu or pfu titre of a viral solution are well known in the art. For retroviruses, dosages in the region of $10^5$ to $10^6$ cfu/ml are particularly preferred.

For pseudotyped retroviruses, dosages in the region of $10^7$ cfu/ml are particularly preferred. For adenoviruses, dosages in the region of $10^9$ pfu/ml are particularly preferred.

For the delivery of MGF polypeptides of the invention suitable doses include doses of from 1 to 1000 µg, from 10 to 100 µg, from 100 to 500 µg and from 500 to 1000 µg. Dosage schedules will also vary according to, for example the route of administration, the species of the recipient and the condition of the recipient. However, MGF polypeptide will typically be given rapidly after the ischemic incident overload, or mechanical as discussed above. Optionally, further doses may be spread over periods of e.g. days, weeks or months. As discussed above, however, delivery by means of polynucleotides that are expressed in vivo is advantageous for long term treatment because it minimises the need for injections into the subject.

EXAMPLES

To investigate the regulation of MGF in cardiac muscle we have used a number of in vivo and in vitro models. To confirm the function of MGF, we have over expressed the MGF gene in cardiac muscle cells in a series of "gain of function experiments".

Figure 1:
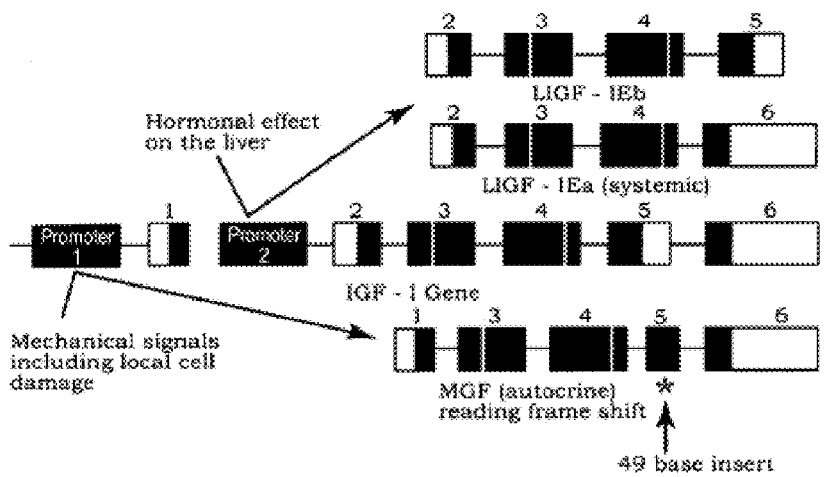
FIG. 1: Alternative splicing of the IGF-I gene
Figure 1A:
Figure 1B:
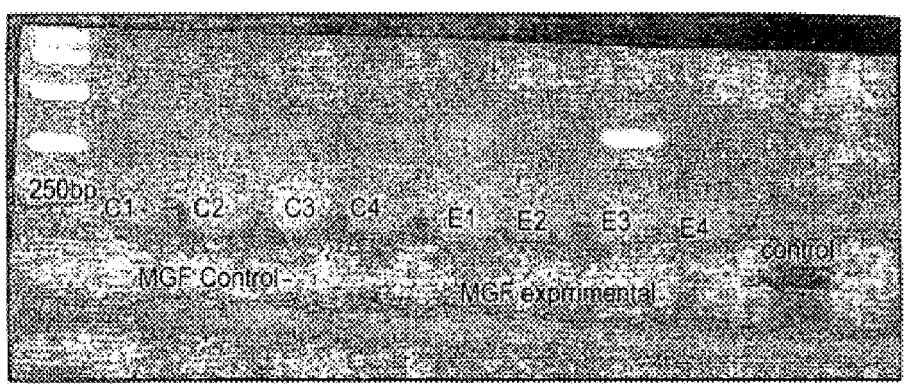

Example 1: Induction of MGF Expression In Vivo During Functional Ischemia and Overload Using reverse transcriptase PCR (RT-PCR) as in Yang et al (1996) and with the same specific oligonucleotide primers, we have shown that MGF is strongly expressed around the infracted area following ischemia in the rat and sheep heart (FIG. 1B).

In an ischemic situation, the surviving cardiomyocytes near to the region of the infarct become functionally overloaded so it is difficult to dissociate the two causes of cell death, i.e. deprivation of oxygen in the blood supply and subsequently increased mechanical strain on the remaining myocytes after some have been killed by oxygen depriva- tion. By placing a small ligature around the aorta (aortic banding; Ding et al (2000)) there is an increase in the amount of work the heart has to do to eject blood in order to maintain a constant blood pressure. This is referred to as an increase in after-load and is seen in patients who suffer from hypertension, and aortic occlusion (build up plaque on the walls of the aorta). Since the heart has to work harder, the compensatory response of the muscle is to hypertrophy in order to match the demands.

We have performed such aortic banding on mice to determine whether the expression of MGF is increased in this model of cardiac hypertrophy. In FIG. 2, the results are shown from groups of 3 mice banded for 7 days compared to sham-operated controls. FIG. 2 shows that MGF expression is markedly induced in functionally overloaded cardiomyocytes. Conversely, expression of liver-type IGF-I was not found to increase following banding.

ANF is an embryonic marker gene that is up regulated in hypertrophic conditions. It can be seen that the banding induced ANF expression indicating cardiac hypertrophy in this model. Also, Bax gene expression is up regulated during apoptosis and in pathological situations and this did not occur in the aortic-banded mice by 7 days. This data shows that MGF expression is increased by functional overload and that, in contrast to the situation for liver-type IGF-I, this expression coincides with the immediate recovery stage after overload. We detected similar changes just following transient ischemia in the rat and the sheep and the expression of MGF was found to be high near to the area of the infarct where the cardiomyocytes are subjected to mechanical overload (see below).

Example 2: Overexpression of MGF In Vitro in Primary Cardiac Myocytes

To further confirm the role of MGF in cardiac compensation we increased MGF expression in primary myocardiocytes. This was achieved by transfecting a plasmid containing the MGF cDNA into primary cultures of cardiac myocytes prepared from neonatal mice (Goldspink et al (1997)).

The initial assay following the transfection was to determine whether there was a change in the number of cells. Myocytes are terminally differentiated cells that do not undergo cell division once committed to myocyte lineage. An increase in the number of cells (hyperplasia) could account for increases in gene expression that were to be assayed and thereby suggest that MGF may not be involved in cardiac hypertrophy. Unlike the situation in skeletal muscle, there was no increase in the number of cells in any of the conditions following transfection. Therefore it can be concluded that the role of MGF in the myocardium is not principally to induce cell division.

RNA was extracted from the cells following transfection (after 72 hours) and was used to assay the expression of the embryonic hypertrophic marker, ANF. Shown in FIG. 2 is the quantitative data derived from the real-time RT-PCR to monitor the level of expression of these growth/repair marker genes in the transfected myocytes. Increased expression of MGF, without a corresponding increase in L.IGF-I expression, shows that it is the MGF isoform that is induced under apoptotic conditions.

Example 3: Induction of MGF Expression in Response to Signal Transduction Pathway Activation In order to investigate which signal appear to modulate MGF expression in cardiac myocytes, several drugs were applied to cardiomyocyte cultures. These in turn activate signal transduction molecules either directly or indirectly through receptor coupled molecules. One such drug is phorbol myristate acetate (PMA), a phorbol ester that specifically activates the Protein Kinase C family of serine/threonine signaling kinases. As shown in FIG. 4, a brief exposure to PMA (200 nM), brings about a significant increase in the expression of the endogenous MGF gene. When the amount of MGF is compared to the amount of liver-type IGF in the control conditions, there is substantially less in the cardiac myocytes. However, the level of MGF is significantly increased in response to PMA whereas the level of IGF does not change (FIG. 5A). When the same experiment was repeated but the PMA was added to myocyte cultures in which the media had not been changed for 24 hours prior to the addition of the PMA, the increase in MGF expression is even greater than when PMA is added along with fresh media (FIG. 5B).

These data shows that PMA, an activator of protein kinase C, induces the expression of the endogenous MGF gene in cardiac myocytes. In the condition in which the media was unchanged the environment is one of increased pH and decreased nutrients. In some respects, this is a similar environment that a myocyte may exist in following an ischemic event, when the blood flow to a region of the heart is interrupted. Under these conditions it can be seen that MGF expression increases even more. This suggests that MGF is activated by ischemia and that one of the signal transduction molecules responsible is protein kinase C. Activation of the protein kinase C family has been implicated in response to a number of hypertrophic and pathologic stimuli in the heart. These signaling molecules have also been implicated to play a role in events that bring about apoptosis (cell death) in cardiac myocytes.

These experiments again show that IGF-I and MGF are different growth factors that have different signaling pathways, and suggest that it is the MGF isoform whose expression is decisive following ischemia.

Example 4: Induction of MGF Expression During Apoptosis

To determine whether MGF is activated under conditions that bring about apoptosis, cardiac myocytes were cultured in the presence of sorbitol. This places the cells under osmotic stress which causes them to swell and eventually die. Initially, myocytes were cultured in defined media minus serum for 24 hours before the addition of sorbitol. Following exposure to sorbitol, RNA was extracted and gene expression was assayed with real time RT-PCR. Shown in FIG. 5 are the changes in MGF and IGF-I gene expression after a short exposure (4 hours) to sorbitol. The expression of MGF can be initially seen to increase whereas IGF does not change. Following longer exposure to sorbitol (24 hours), MGF expression is the same as control whereas IGF is increased. This demonstrates the different kinetics of MGF as compared to IGF-I, and further supports the idea that it is MGF expression that is decisive following ischemia/mechanical overload. Increased Bax gene expression also indicated that the cells are undergoing apoptosis, which was further demonstrated by the appearance of DNA fragmentation in the sorbitol treated cultures after 24 hours.

Figure 6:
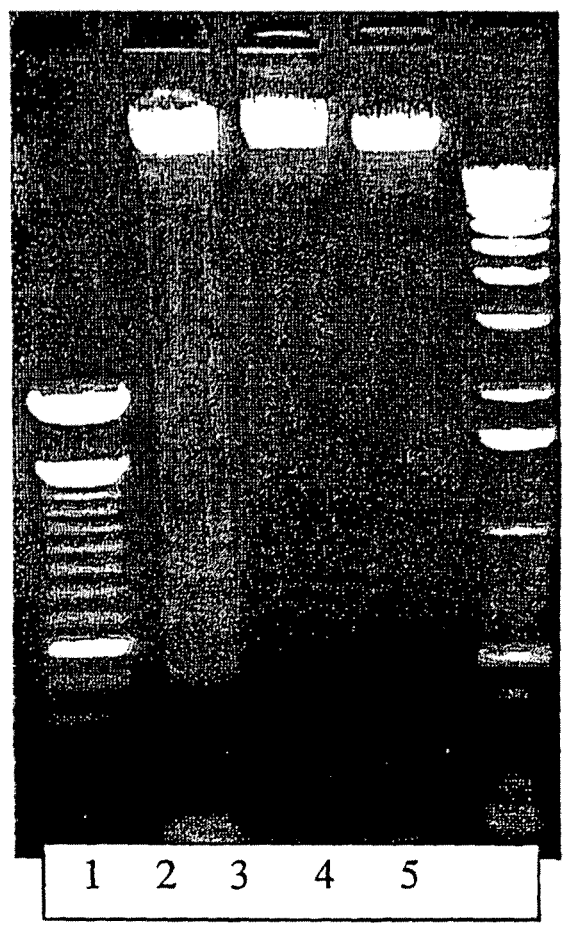

To further determine the role of MGF in the prevention of apoptosis, a cardiac-like cell line (H9C2) (Kimes et al (1976), and commercially available from American Type Culture Collection PO Box 1549, Manassas, Va. 20108, USA) was stably transfected with MGF and liver-type IGF cDNA using a pcDNA3.1/NT-GFP vector (Invitrogen Corporation, 1600 Faraday Avenue, Carlsbad, Calif. 92008, USA) and the techniques of Southern et al (1982). The stably transfected cell lines plus the non-transfected control were then treated with sorbitol for 24 hours and DNA extracted to analyze the extent of DNA fragmentation, which is an indicator of apoptosis. Shown in FIG. 6, is the DNA analysis following 24 hours of treatment with sorbitol. It can be clearly seen, that the DNA extracted from the control (non-transfected) cells shows the characteristic pattern of fragmentation associated with apoptosis. The cells stably transfected with the MGF and IGF cDNA do not show any sign of DNA fragmentation indicating that they have not undergone apoptosis. This protective feature has previous been described for IGF in cardiac muscle (Yamashita et al, 2001), but has never been described for MGF.

These data show that the insulin like growth factor splice variant, MGF is activated in response to cardiac tissue damage and that it has a repair function. Thus its administration has a cardio-protective effect which will be beneficial to the ischemic/overloaded heart.

Example 5: Evidence that MGF and Peptides Accumulate Differently within Cardiomyocytes This indicates that the MGF receptor is probably in the nucleus whilst the IGF-IEa receptor is non-nuclear, and also that the biological actions of the two splice variants are different.

In order to express MGF in primary cultures of cardiac myocytes an adenoviral mediated gene expression—the AdEasy Adenoviral Vector Systems (Stratagene)—was used to express MGF and L.IGF cDNA in isolated myocytes. The MGF L.IGF were sequences were in frame with the Green Fluorescent Protein (GP5), which is downstream of the CMV promoter of the pcDNA 3.1/NT-GFP vector (Invitrogen). The whole cassette was removed and the ligated into the pShuttle vector in order to produce the virus. This vector carries the homology regions for the homologous recombination with the pAdEasy vector, which is derived from the human adenovirus serotype 5. The virus is rendered replication deficient by deletion of the packaging and host immunity genes (E1 and E3). The resulting viral/vector construct was used to transfect 293 packaging cells to produce a primary viral stock. The primary stock was used to amplify the virus through a series of infections in 293 cells before the final viral stock was purified by CsCl ultra centrifugation. The final viral titer was quantified via a spectrophotometric method, which yielded a purified viral titer in the order of $10^{11}$-$10^{12}$ particles/ml. These particles were used to infect primary myocytes in the range of $10^8$-$10^9$ particles/ml.

A number of striking observations were made following 24 hrs of viral infection into primary cardiac myocytes. Shown in the FIG. 1 is the different intracellular localization of the MGF-GPF virus compared to the IGF-GFP virus. Since a fusion protein was made with the GFP, visualization of the infected cells with a fluorescent microscope demonstrated a discrete nuclear localization of the MGF-GFP virus (FIG. 14A). Contrary to this, The L.IGF-GFP virus while also being present in the nucleus was additionally expressed throughout the cytoplasm of the cell as well (FIG. 14B).

To confirm that the nuclei of the myocytes were expressing the MGF, virus cells were counter stained with dia (DAPI), which binds to chromatin in the nucleus and can be viewed with fluorescence. Shown in FIG. 15 are the results of the staining. The pattern of staining confirms MGF expression in the nucleus.

Following the initial period of infection, myocytes were infected for longer periods to determine the effects of MGF over expression. Cells were plated and infected with the MGF virus and a GFP expressing virus as a control for 48 hrs. Following infection cells were fixed in paraformaldehyde and counter stained with Texas Red conjugated phalloidin (Molecular Probes) to visualize the myofilaments and DAPI to visualize the nucleus. Shown in FIG. 16 are the results of a 48-hour infection. In the control myocytes without infection the presence of striated myofilaments can be seen with the phalloidin stain (FIG. 16A). Likewise, in myocytes infected with a GFP expressing control virus the myofilaments remain intact based upon their striated appearance (FIG. 16B). However in the MGF infected myocytes, there were no striations in the myofilaments when stained with the phalloidin suggesting the myofilament proteins have been disassembled (FIGS. 16C and D).

To further explore the apparent disassembly of the myofilament proteins, the levels mRNA expression of a number of myofilament proteins were analyzed using RT-PCR. Total RNA was extracted from control myocytes and myocytes infected for 48 hrs with the MGF virus. The expression of several myofilament proteins was looked at using conventional RT-PCR. Shown in FIG. 17 are the results following electrophoresis of the thick filament proteins (myosin heavy chain and light chains) and the thin filament proteins (actin, tropomyosin and troponin T). A down regulation of the thick filament proteins can be clearly seen in the MGF infected cells, whereas the thin filament proteins do not appear to be affected. Four separate cultures were used as controls without infection and four separation cultures infected with the MGF virus.

Further analysis of the suppression of thick filament protein expression was performed using quantitative RT-PCR. In FIG. 18 the expression of the α-myosin heavy chain (the predominant isoform expressed in the rodent heart) is decreased by over 100 fold in the MGF infected myocytes.

These data show that expression of MGF is localized to nucleus of cardiac myocytes whereas IGF expression is throughout the cell. Prolonged expression of MGF in cardiac myocytes is associated with the suppression of the thick filament proteins of the myofilaments but not the thin filament proteins. This results in a loss of the myofilament cross-striations within the myocyte but leaves the actin cytoskeleton intact. The selective down regulation of muscle specific proteins essentially acts to dedifferentiate the myocyte, which may be a necessary step to enter the cell cycle from its terminally differentiated state. Therefore, it can be seen that MGF expression results in remodelling of the infracted region, i.e. that, according to the invention, MGF will be useful in preventing or limiting myocordial damage in response to ischemia or mechanical overload of the heart.

Example 6: Time Course of Damage-Regeneration and Expression of MGF an IGF-IEa Following Muscle Damage This example demonstrates that MGF and L.IGF-I have different expression kinetics. Muscle damage was induced by mechanical means and via a myotoxic agent. The results clearly showed that MGF is produced shortly after the insult whereas L.IGF-IEa was expressed several days later.

Muscle damage was induced by mechanical means, namely stretch and stimulation, and injection of the myotoxic agent bupivacaine.

In FIG. 19, the mean percentage of damage-regenerating muscle fibre area in relation to the whole muscle section is assessed in both damaged models.

There is a continuing decrease in the damaged-regenerating area after 4 days following bupivacaine injection and 5 days after stretch and stimulation where maximal damage was present in both (FIG. 19A). The same pattern was seen with the embryonic myosin heavy chain staining the regenerating area in both models (FIG. 19B). Two-way analysis of variance (ANOVA) was used to determine significant differences among the means. N=4 for bupivacaine model and N=6 for stretch/stimulation model for each time point. Experimental muscles were compared with those of the untreated animals at zero time and all differences were significant at the P<0.01 up to 15 days post-injury.

FIG. 20 shows the results of investigation of mRNA levels of MGF and IGF-IEa isoforms in the two models of muscle damage.

MGF was maximally expressed as early as 1 day following stretch and stimulation and 4 days following bupivacaine injection (FIG. 20A), whereas liver-type IGF-IEa was maximally expressed later at 7 and 11 days following injury (FIG. 20B). Two-way analysis of variance (ANOVA) was used to determine significant differences among the means. N=6 for stretch/stimulation model and N=4 for bupivacaine model for each time point. MGF measurements were significant at P<0.01 levels for up to 5 days and liver-type IGF-IEa for up to 11 days.

This provides further evidence that it is the MGF isoform rather IGF-IEa isoform that offers cardioprotection.

REFERENCES

Buerke et al (1995) *Proceedings of the National Academy of Sciences of the United States of America* 92:8031-8035
Chew et al (1995) *Endocrinology* 136, No. 5
Ding et al (2000) *Circulation* 101:2854-2862
Fazio et al (1996) *N. Engl. J. Med.* 334: 809-814
Goldspink et al (1997) *J. Cell Sci.* 110:2969-2978
Kimes et al (1976) *Exp. Cell. Res.* 98:367-381
Lakshmana et al (1990) *Biochemical & Biophysical Research Communications* 173, 902-911
McKoy et al (1999) *J. Physiol.* 516.2, 573-592
Matthews et al (1999) *J Endocrinol.* 163: 433-445
Siegfried et al (1992) *Proceedings of the National Academy of Sciences of the United States of America* 39: 8107-8111
Sha et al (1991) *J. Cell Biology* 114: 827-839
Skarli et al (1998) 192 *J. Physiol.* 509P
Southern et al (1982) *J. Mol. Appl. Genet.* 1:327-341
Thuesen et al (1988) *Dan. Med. Bull.* 35: 193-196
Tian et al (1999) *Endocrinology* 140: 3387-3390
Wells D J and Goldspink G. (1992) *FEBS Letters* 306: 203-205
Wolff et al (1990) *Science* 247: 1465-1468
Yamashita et al (2001) *Circ Res.* 30; 88(6):609-614
Yang et al (1996) *J. Muscle Res. Cell Motil.* 17: 487-495

The invention claimed is:

1. A method for limiting myocardial damage in response to a heart attack, comprising:
   administering to a subject in need thereof a Mechano Growth Factor (MGF) polypeptide in an amount effective to limit myocardial apoptosis,
   wherein the MGF polypeptide that is administered comprises:
   (a) an amino acid sequence selected from the group consisting of SEQ ID NO:2 and SEQ ID NO:4; or
   (b) an amino acid sequence selected from the group consisting of the amino acid sequence encoded by exons 5 and 6 of SEQ ID NO:1; and the amino acid sequence encoded by exons 4, 5 and 6 of SEQ ID NO:3.

2. The method of claim 1, wherein the MGF polypeptide is unglycosylated.

3. The method of claim 1, wherein the amino acid sequence encoded by exons 5 and 6 is the amino acid sequence of amino acids 87-110 of SEQ ID NO:2 or amino acids 87-111 of SEQ ID NO:4.

4. The method of claim 1, wherein the MGF polypeptide induces a hypertrophic phenotype in cardiac muscle cells.

5. The method of claim 1, wherein the MGF polypeptide is formulated for intramuscular administration.

6. The method of claim 1, wherein the polypeptide is administered within 5 hours of the heart attack.

7. The method of claim 6, wherein the polypeptide is administered within 2 hours of the heart attack.

8. The method of claim 7, wherein the polypeptide is administered within 60 minutes of the heart attack.

9. The method of claim 8, wherein the polypeptide is administered within 30 minutes, 15 minutes, 10 minutes, or 5 minutes of the heart attack.

* * * * *